(12) United States Patent
Dantanarayana

(10) Patent No.: US 11,147,940 B2
(45) Date of Patent: *Oct. 19, 2021

(54) GAS WASHOUT VENT FOR PATIENT INTERFACE

(71) Applicant: ResMed Pty Ltd, Bella Vista (AU)

(72) Inventor: Muditha Pradeep Dantanarayana, Sydney (AU)

(73) Assignee: ResMed Pty Ltd, Bella Vista (AU)

(*) Notice: Subject to any disclaimer, the term of this patent is extended or adjusted under 35 U.S.C. 154(b) by 0 days.

This patent is subject to a terminal disclaimer.

(21) Appl. No.: 16/803,147

(22) Filed: Feb. 27, 2020

(65) Prior Publication Data

US 2020/0188628 A1 Jun. 18, 2020

Related U.S. Application Data

(63) Continuation of application No. 15/512,149, filed as application No. PCT/AU2015/050560 on Sep. 18, 2015, now Pat. No. 10,695,527.

(Continued)

(30) Foreign Application Priority Data

Sep. 18, 2014 (AU) .............................. 2014903730

(51) Int. Cl.
*A61M 16/06* (2006.01)
*A61M 16/22* (2006.01)
*A61M 16/08* (2006.01)

(52) U.S. Cl.
CPC ............ *A61M 16/22* (2013.01); *A61M 16/06* (2013.01); *A61M 16/0622* (2014.02);

(Continued)

(58) Field of Classification Search
CPC .. A61M 16/22; A61M 16/06; A61M 2205/42; A61M 16/1065

See application file for complete search history.

(56) References Cited

U.S. PATENT DOCUMENTS 4,612,926 A * 9/1986 Boiarski ............... A61M 16/12
128/200.21
4,782,832 A 11/1988 Trimble et al.
(Continued)

FOREIGN PATENT DOCUMENTS

CN 1901962 1/2007
CN 101380497 3/2009
(Continued)

OTHER PUBLICATIONS

Notice of Reasons for Rejection dated Feb. 25, 2020 in Japanese Application No. 2017-515131, with English translation, 17 pages.

(Continued)

*Primary Examiner* — Margaret M Luarca
(74) *Attorney, Agent, or Firm* — Nixon & Vanderhye P.C.

(57) ABSTRACT

A gas washout vent, and a patient interface with the gas washout vent, configured to allow patient-exhaled $CO_2$ to flow to an exterior of the plenum chamber to minimise rebreathing of exhaled $CO_2$ by the patient, the gas washout vent including at least one outlet orifice; a diffusing member at least partly covering the outlet orifice; and a blocking member having an air-impermeable material, the blocking member preventing gas exiting from the outlet orifice from flowing straight through the diffusing member.

24 Claims, 30 Drawing Sheets

Related U.S. Application Data

(60) Provisional application No. 62/141,342, filed on Apr. 1, 2015.

(52) U.S. Cl.
CPC .... *A61M 16/0666* (2013.01); *A61M 16/0683* (2013.01); *A61M 16/0816* (2013.01); *A61M 16/0825* (2014.02); *A61M 16/0616* (2014.02); *A61M 2202/0225* (2013.01); *A61M 2205/42* (2013.01)

(56) References Cited

U.S. PATENT DOCUMENTS

| | | | |
|---|---|---|---|
| 4,944,310 | A | 7/1990 | Sullivan |
| 6,532,959 | B1 | 3/2003 | Berthon-Jones |
| 6,581,594 | B1 | 6/2003 | Drew et al. |
| 7,866,944 | B2 | 1/2011 | Kenyon et al. |
| 8,636,479 | B2 | 1/2014 | Kenyon et al. |
| 8,638,014 | B2 | 1/2014 | Sears et al. |
| 8,733,349 | B2 | 5/2014 | Bath et al. |
| 10,695,527 | B2 * | 6/2020 | Dantanarayana ............ A61M 16/0825 |
| 2001/0003327 | A1 * | 6/2001 | Sanders ............. G11B 33/0494 206/308.1 |
| 2006/0266365 | A1 * | 11/2006 | Stallard ................. A61M 16/08 128/207.13 |
| 2009/0044808 | A1 | 2/2009 | Guney et al. |
| 2009/0044810 | A1 | 2/2009 | Kwok et al. |
| 2009/0050156 | A1 * | 2/2009 | Ng .................. A61M 16/08 128/205.24 |
| 2010/0000534 | A1 | 1/2010 | Kooij et al. |
| 2010/0083969 | A1 * | 4/2010 | Crumblin ............. A61M 16/06 128/206.21 |
| 2011/0011397 | A1 | 1/2011 | Ziv et al. |
| 2011/0180071 | A1 * | 7/2011 | Veliss ............... A61M 16/0825 128/206.21 |
| 2011/0247625 | A1 | 10/2011 | Boussignac |
| 2012/0132209 | A1 * | 5/2012 | Rummery ............. A61M 16/06 128/205.25 |
| 2012/0304985 | A1 | 12/2012 | Lalonde |
| 2014/0283831 | A1 * | 9/2014 | Foote .................. A61M 16/026 128/204.19 |
| 2014/0366882 | A1 | 12/2014 | Ng et al. |
| 2015/0209541 | A1 * | 7/2015 | Harwood ........... A61M 16/0666 128/205.25 |
| 2016/0008558 | A1 * | 1/2016 | Huddart ............ A61M 16/0683 128/205.25 |
| 2016/0263409 | A1 * | 9/2016 | Lee .................... B29C 45/14065 |
| 2016/0310687 | A1 | 10/2016 | McAuley et al. |
| 2017/0281898 | A1 | 10/2017 | Dantanarayana |
| 2017/0291004 | A1 | 10/2017 | Ng et al. |

FOREIGN PATENT DOCUMENTS

| | | |
|---|---|---|
| CN | 101732787 | 6/2010 |
| CN | 102458547 | 5/2012 |
| CN | 102458548 | 5/2012 |
| CN | 103476446 | 12/2013 |
| CN | 103961775 | 8/2014 |
| EP | 1 163 923 | 12/2001 |
| EP | 2 027 880 | 2/2009 |
| JP | 2002-95751 A | 4/2002 |
| JP | 2009-50707 A | 3/2009 |
| JP | 2011-218175 A | 11/2011 |
| JP | 2012-531977 A | 12/2012 |
| WO | WO 98/004310 A1 | 2/1998 |
| WO | WO 98/034665 A1 | 8/1998 |
| WO | WO 2000/078381 A1 | 12/2000 |
| WO | WO 02/051486 A1 | 7/2002 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2008/011682 A1 | 1/2008 |
| WO | WO 2009/052560 A1 | 4/2009 |
| WO | WO 2010/135785 A1 | 12/2010 |
| WO | WO 2012/109704 A1 | 8/2012 |
| WO | WO 2012/171072 A1 | 12/2012 |
| WO | WO 2013/020167 A1 | 2/2013 |
| WO | 2014/110622 | 7/2014 |
| WO | WO 2014/129913 A1 | 8/2014 |
| WO | WO 2016/041019 A1 | 3/2016 |
| WO | WO 2016/119018 A1 | 8/2016 |

OTHER PUBLICATIONS

International Search Report for PCT/AU2015/050560 dated Nov. 24, 2015, 9 pages.

Written Opinion of the ISA for PCT/AU2015/050560 dated Nov. 24, 2015, 6 pages.

"*Respiratory Physiology*", by John B. West, Lippincott Williams & Wilkins, 9$^{th}$ edition published 2012 (8 pages).

Feb. 20, 2018 Extended Search Report issued in European Application No. 15841442.5.

Chinese Office Action and its English translation for Chinese Application No. 2015800506779, 14 pages, dated Jan. 22, 2019.

Notice of Reasons for Rejection dated Jun. 10, 2019 in Japanese Application No. 2017-515131, with English translation, 26 pages.

* cited by examiner

Nose - Anterolateral view

GAS WASHOUT VENT FOR PATIENT INTERFACE

CROSS REFERENCE TO RELATED APPLICATIONS

This application is a continuation application of U.S. patent application Ser. No. 15/512,149, filed 17 Mar. 2017, which is the U.S. national phase of International Application No. PCT/AU2015/050560 filed 18 Sep. 2015, which designated the U.S. and claims priority to U.S. Provisional Application No. 62/141,342, filed 1 Apr. 2015 and AU Provisional Application No. 2014903730, filed 18 Sep. 2014, the entire contents of each of which are hereby incorporated by reference in their entirety.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

BACKGROUND OF THE TECHNOLOGY

1.1 Field of the Technology

The present technology relates to one or more of the detection, diagnosis, treatment, prevention and amelioration of respiratory-related disorders. The present technology also relates to medical devices or apparatus, and their use.

1.2 Description of the Related Art

1.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

1.2.2 Therapy

Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. NIV has been used to treat CSR, OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

1.2.3 Diagnosis and Treatment Systems

These therapies may be provided by a treatment system or device. Systems and devices may also be used to diagnose a condition without treating it.

A treatment system may comprise a Respiratory Pressure Therapy Device (RPT device), an air circuit, a humidifier, a patient interface, and data management.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

1.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g., because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design will fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the patient's face when force is applied to the patient interface with the seal-forming portion in confronting engagement with the patient's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming portion does not match that of the patient, it may crease or buckle in use, giving rise to leaks.

Another type of seal-forming portion may comprise a friction-fit element, e.g., for insertion into a naris, however some patients find these uncomfortable.

Another form of seal-forming portion may use adhesive to achieve a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT' LT nasal pillows); International Patent Applications WO 2005/063, 328 and WO 2006/130,903 (describing amongst other things aspects of the ResMed Limited MIRAGE LIBERTY' full-face mask); International Patent Application WO 2009/052, 560 (describing amongst other things aspects of the ResMed Limited SWIFT™ FX nasal pillows).

1.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

1.2.3.1.3 Vent Technologies

Some forms of patient interface systems may include a vent to allow the washout of exhaled carbon dioxide. The vent may allow a flow of gas from an interior space of the patient interface, e.g., the plenum chamber, to an exterior of the patient interface, e.g., to ambient. The vent may comprise an orifice and gas may flow through the orifice in use of the mask. Many such vents are noisy. Others may become blocked in use and thus provide insufficient washout. Some vents may be disruptive of the sleep of a bed-partner 1100 of the patient 1000, e.g., through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

| Table of noise of prior masks (ISO 17510-2: 2007, 10 cmH$_2$O pressure at 1 m) | | | | |
|---|---|---|---|---|
| Mask name | Mask type | A-weighted sound power level dB(A) (uncertainty) | A-weighted sound pressure dB(A) (uncertainty) | Year (approx.) |
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

((*) one specimen only, measured using test method specified in ISO3744 in CPAP mode at 10 cmH$_2$O)

Sound pressure values of a variety of objects are listed below.

| Object | A-weighted sound pressure dB(A) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

1.2.3.2 Respiratory Pressure Therapy (RPT) Device

Air pressure generators are known in a range of applications, e.g., industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO3744 in CPAP mode at 10 cmH$_2$O).

| RPT Device name | A-weighted sound power level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

1.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

One form of the present technology comprises a gas washout vent with at least one outlet orifice; a diffusing member covering the outlet orifice; and a blocking member having an air-impermeable material, the blocking member preventing gas exiting from the outlet orifice from flowing straight through the diffusing member.

Another aspect of one form of the present technology is a patient interface for sealed delivery of a flow of air at a continuously positive pressure with respect to ambient air pressure to an entrance to the patient's airways including at least an entrance of a patient's nares, wherein the patient interface is configured to maintain a therapy pressure in a range of about 4 cmH$_2$O to about 30 cmH$_2$O above ambient air pressure in use, throughout the patient's respiratory cycle, while the patient is sleeping, to ameliorate sleep disordered breathing, the patient interface comprising: a sealing structure configured to seal around the entrance to the patient's airways; a positioning and stabilising structure to maintain the sealing structure in sealing contact with an area surrounding the entrance to the patient's airways while maintaining a therapeutic pressure at the entrance to the patient's airways; a plenum chamber configured to be pressurised at a pressure above ambient pressure in use; a gas washout vent configured to allow patient-exhaled CO$_2$ to flow to an exterior of the plenum chamber to minimise rebreathing of exhaled CO$_2$ by the patient, the gas washout vent including at least one outlet orifice; a diffusing member at least partly covering the outlet orifice; and a blocking member having an air-impermeable material, the blocking member preventing gas exiting from the outlet orifice from flowing straight through the diffusing member.

In examples, (a) the diffusing member and the blocking member are configured to direct the gas exiting from the outlet orifice outward from the diffusing member in an orientation different than the outlet orifice; (b) the diffusing member provides a flow path parallel to a surface of the blocking member that is in contact with the diffusing member; (c) the diffusing member is a porous material; (d) the diffusing member is an open cell foam; (e) the diffusing member is fibrous material; (f) the blocking member is fixed to the diffusing member along a surface of the blocking member that contacts the diffusing member; (g) the surface of the blocking member is opposite the outlet orifice with respect to a thickness of the diffusing member; (h) the patient interface further comprises a plurality of outlet orifices; (i) the diffusing member covers each of the plurality of outlet orifices; (j) an axis defined by a center of the orifice is not perpendicular to a nearest surface of the diffusing member; (k) the air-impermeable material is a flexible material; (l) the air-impermeable material is a rigid material; (m) the patient interface further comprises a channel configured to allow liquid to drain away from the outlet orifice; (n) the orifice is in the channel; (o) the channel has a V-shaped or U-shaped cross-section; (p) the orifice is in a leg of the V-shaped or U-shaped cross section; (q) the blocking member comprises holes configured to redirect the gas exiting from the orifice; (r) the holes include multiple orientations of the holes that are configured to redirect the gas in multiple directions; (s) the diffusing member and the blocking member are removably attached to the plenum chamber; (t) the orifice is sized to result in substantially all of the pressure drop of gas passing through the washout vent and diffusing member when the therapy pressure is applied; (u) the orifice causes choked flow at the therapy pressure; and/or (v) the orifice causes choked flow when the therapy pressure is about 4 cmH$_2$O.

Another aspect of one form of the present technology is a gas washout vent for a patient interface configured to maintain a therapy pressure in a range of about 4 cmH$_2$O to about 30 cmH$_2$O above ambient air pressure in use, throughout a patient's respiratory cycle, while the patient is sleeping, to ameliorate sleep disordered breathing, the gas washout vent comprising: at least one outlet orifice; a diffusing member covering the outlet orifice; and a blocking member having an air-impermeable material, the blocking member preventing gas exiting from the outlet orifice from flowing straight through the diffusing member.

In examples, (a) the diffusing member and the blocking member are configured to direct the gas exiting from the outlet orifice outward from the diffusing member in an orientation different than the outlet orifice; (b) the diffusing member provides a flow path parallel to a surface of the blocking member that is in contact with the diffusing member; (c) the diffusing member is a porous material; (d) the diffusing member is an open cell foam; (e) the diffusing member is fibrous material; (f) the blocking member is fixed to the diffusing member along a surface of the blocking member that contacts the diffusing member; (g) the surface of the blocking member is opposite the outlet orifice with respect to a thickness of the diffusing member; (h) the gas washout vent further comprising a plurality of outlet orifices; (i) the diffusing member covers each of the plurality of outlet orifices; (j) an axis defined by a center of the orifice is not perpendicular to a nearest surface of the diffusing member; (k) the air-impermeable material is a flexible material; (l) the air-impermeable material is a rigid material; (m) the gas washout vent further comprising a channel configured to allow liquid to drain away from the outlet orifice; (n) the orifice is in the channel; (o) the channel has a V-shaped or U-shaped cross-section; (p) the orifice is in a leg of the V-shaped or U-shaped cross section; (q) the blocking member comprises holes configured to redirect the gas exiting from the orifice; (r) the holes include multiple orientations of the holes that are configured to redirect the gas in multiple directions; (s) the diffusing member and the blocking member are removably attachable to the gas washout vent; (t) the orifice is sized to result in substantially all of the pressure drop of gas passing through the washout vent and diffusing member when the therapy pressure is applied; (u) the orifice causes choked flow at the therapy pressure; and/or (v) the orifice causes choked flow when the therapy pressure is about 4 cmH$_2$O.

Another aspect of one form of the present technology is a gas washout vent for a patient interface configured to maintain a therapy pressure in a range of about 4 cmH$_2$O to about 30 cmH$_2$O above ambient air pressure in use, throughout a patient's respiratory cycle, while the patient is sleeping, to ameliorate sleep disordered breathing, the gas washout vent comprising: at least one outlet orifice defining a first axis; a diffusing member covering the outlet orifice; and a blocking member having an air-impermeable material, the blocking member preventing gas exiting from the outlet orifice from flowing straight through the diffusing member and including at least one hole through the blocking member, the hole defining a second axis, wherein the first axis and the second axis are not aligned and not parallel.

In examples, (a) the first axis and the second axis form an angle between 15 and 75 degrees; (b) the first axis and the second axis form an angle between 30 and 60 degrees; (c) the gas washout vent comprises a plurality of the outlet orifice and a plurality of hole; (d) the at least one outlet orifice is formed through a thickness of material and the first axis forms an acute angle with a normal to a surface of the material; the acute angle is between 15 and 75 degrees; and/or (e) the acute angle is between 30 and 60 degrees.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including.

3.1 Treatment Systems

3.2 Respiratory System and Facial Anatomy

Figure 1A:
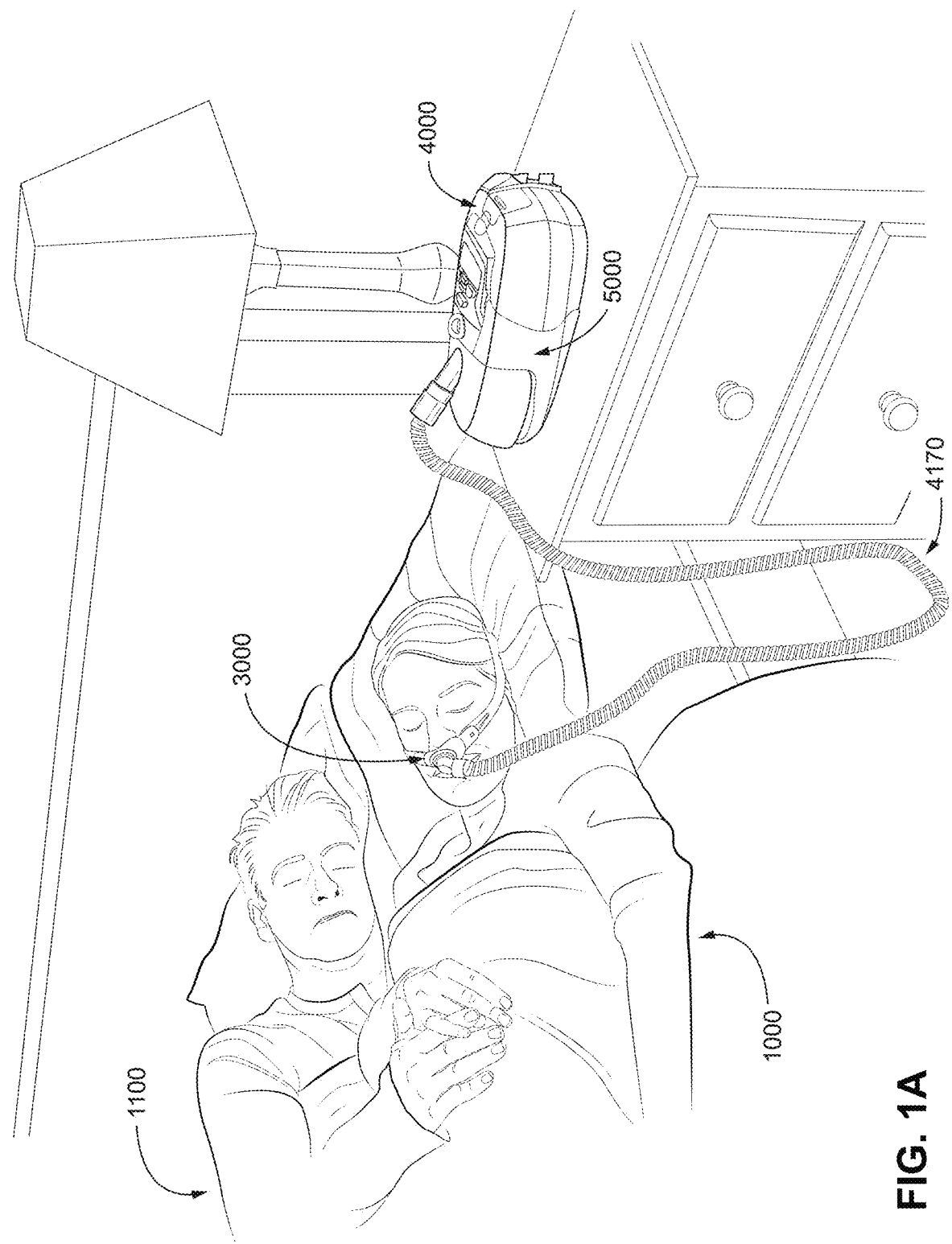
FIG. 1A shows a system including a patient 1000 wearing a patient interface 3000, in the form of a nasal pillows, receiving a supply of air at positive pressure from an RPT device 4000. Air from the RPT device is humidified in a humidifier 5000, and passes along an air circuit 4170 to the patient 1000. A bed partner 1100 is also shown.
Figure 1B:
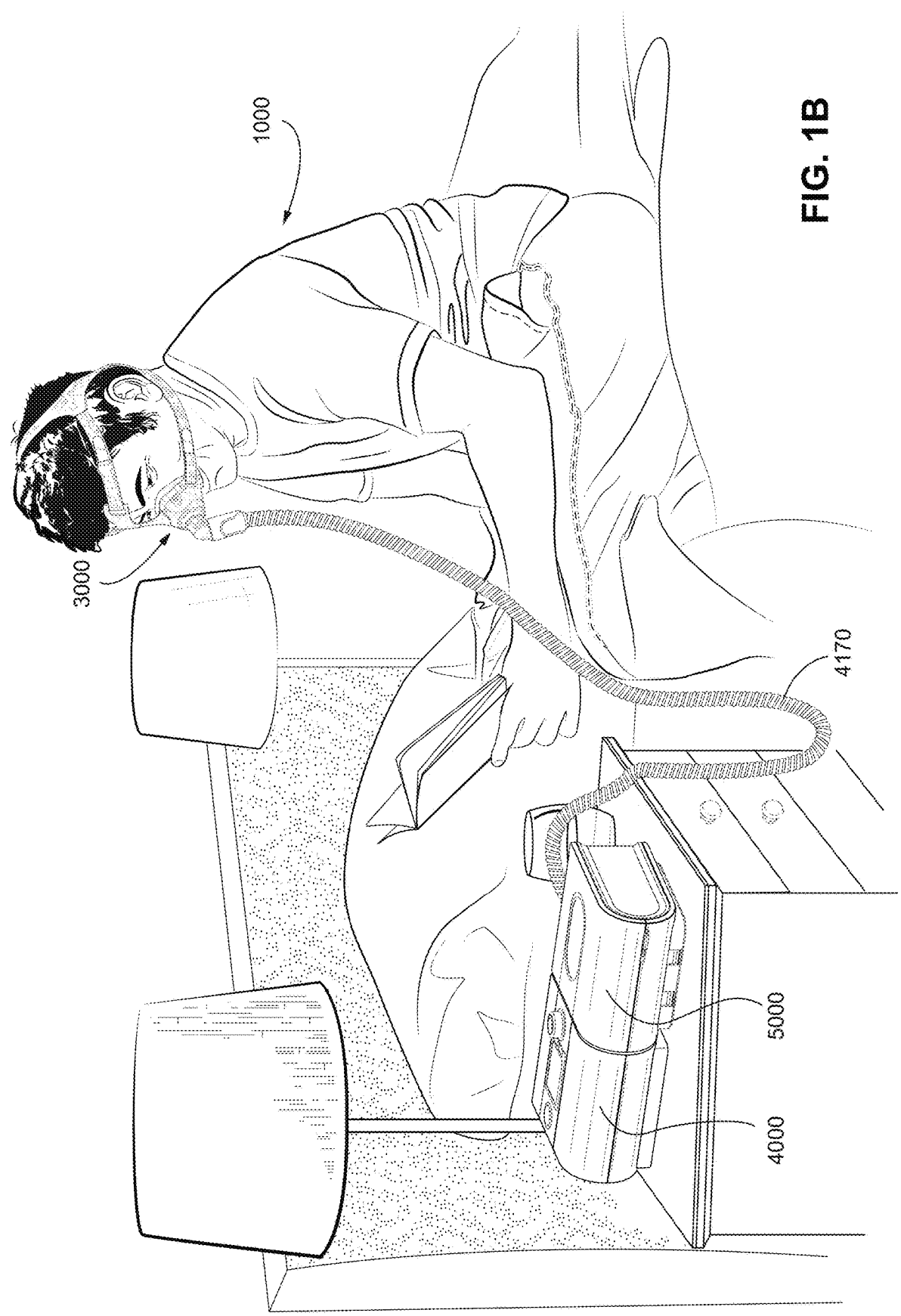
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
Figure 1C:
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1D:
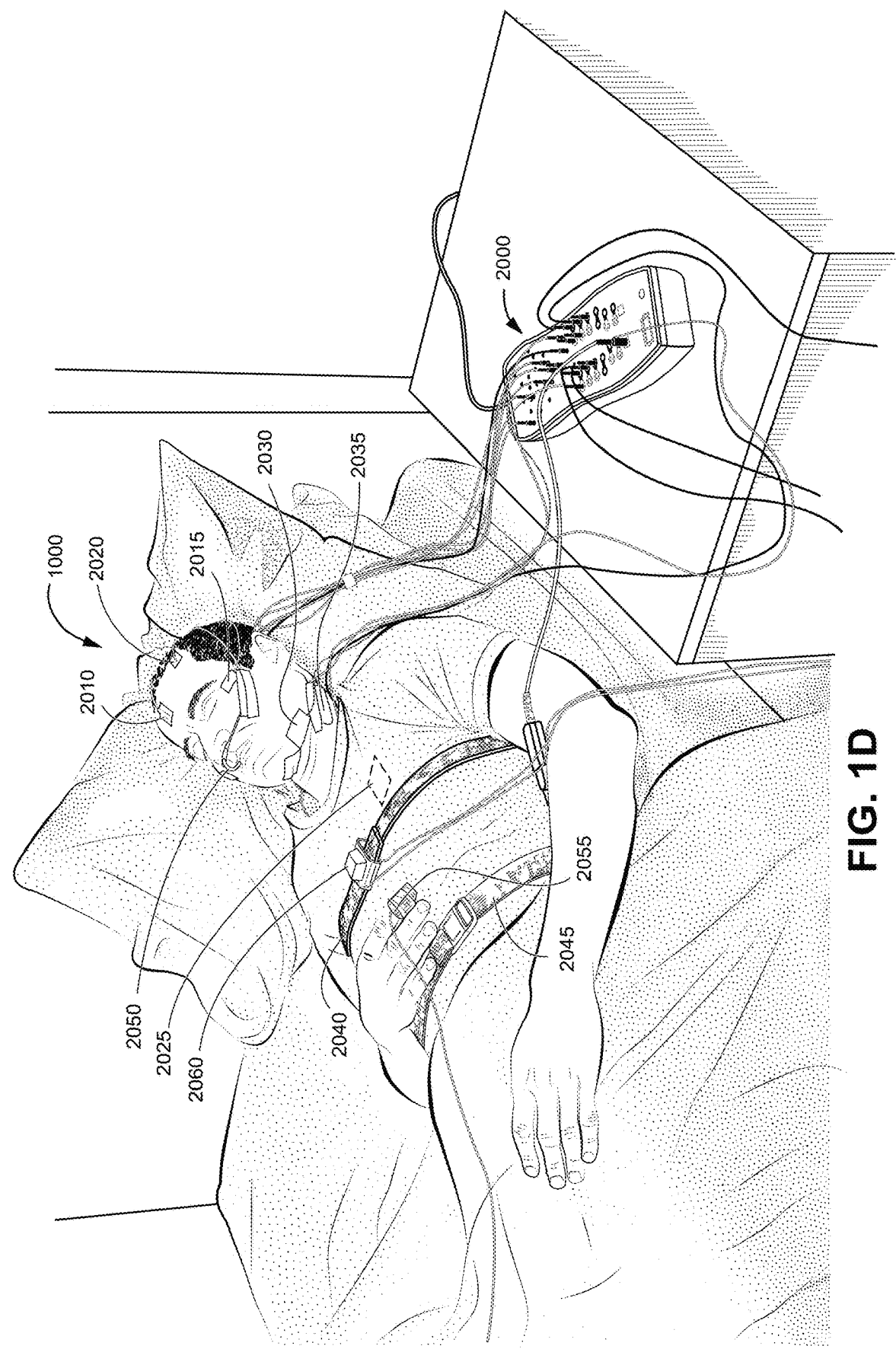
FIG. 1D shows a patient 1000 undergoing polysomnography (PSG).
Figure 2A:
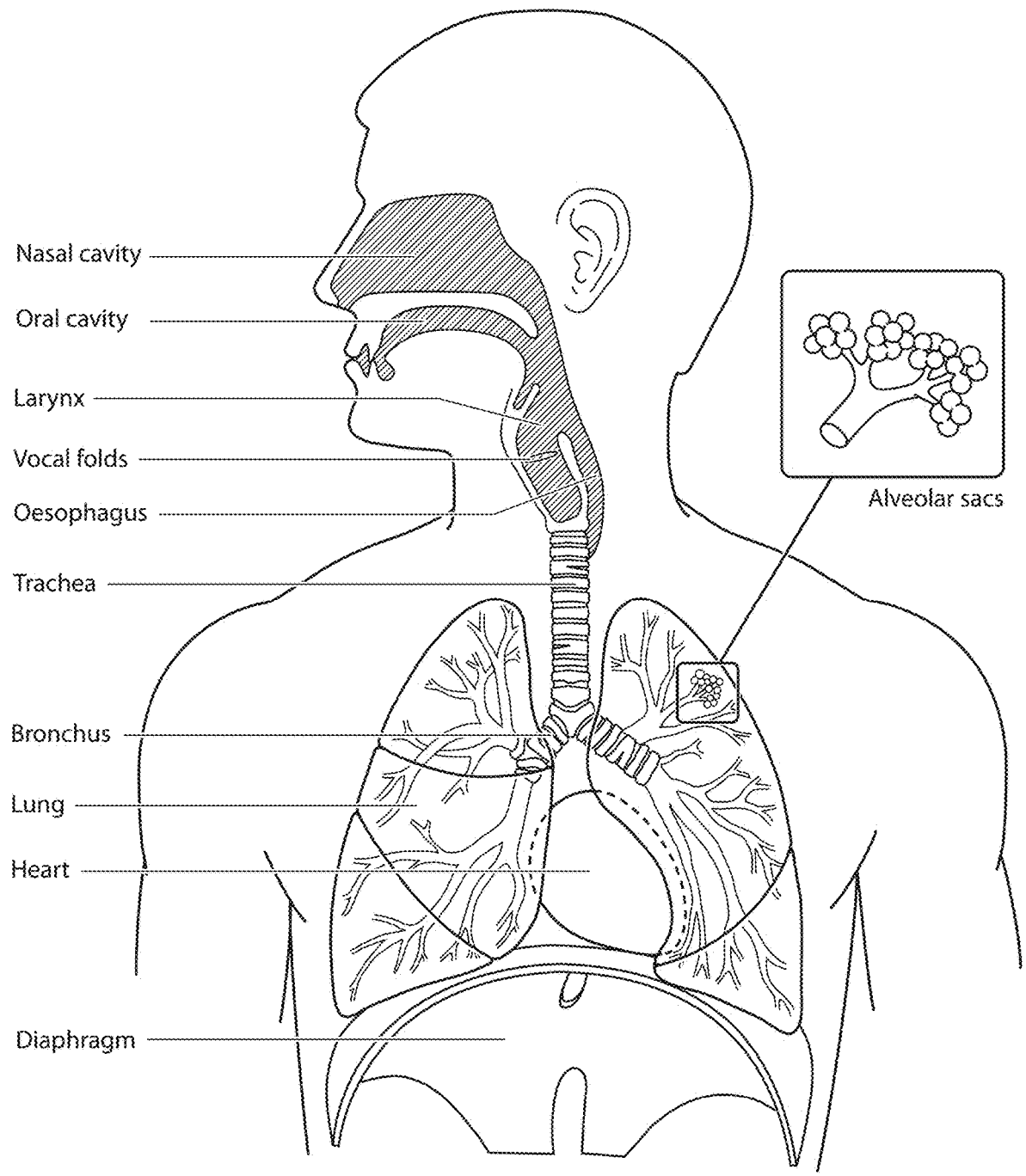

FIG. 2A shows an overview of a human respiratory system including the nasal and oral cavities, the larynx, vocal folds, oesophagus, trachea, bronchus, lung, alveolar sacs, heart and diaphragm.

Figure 2B:
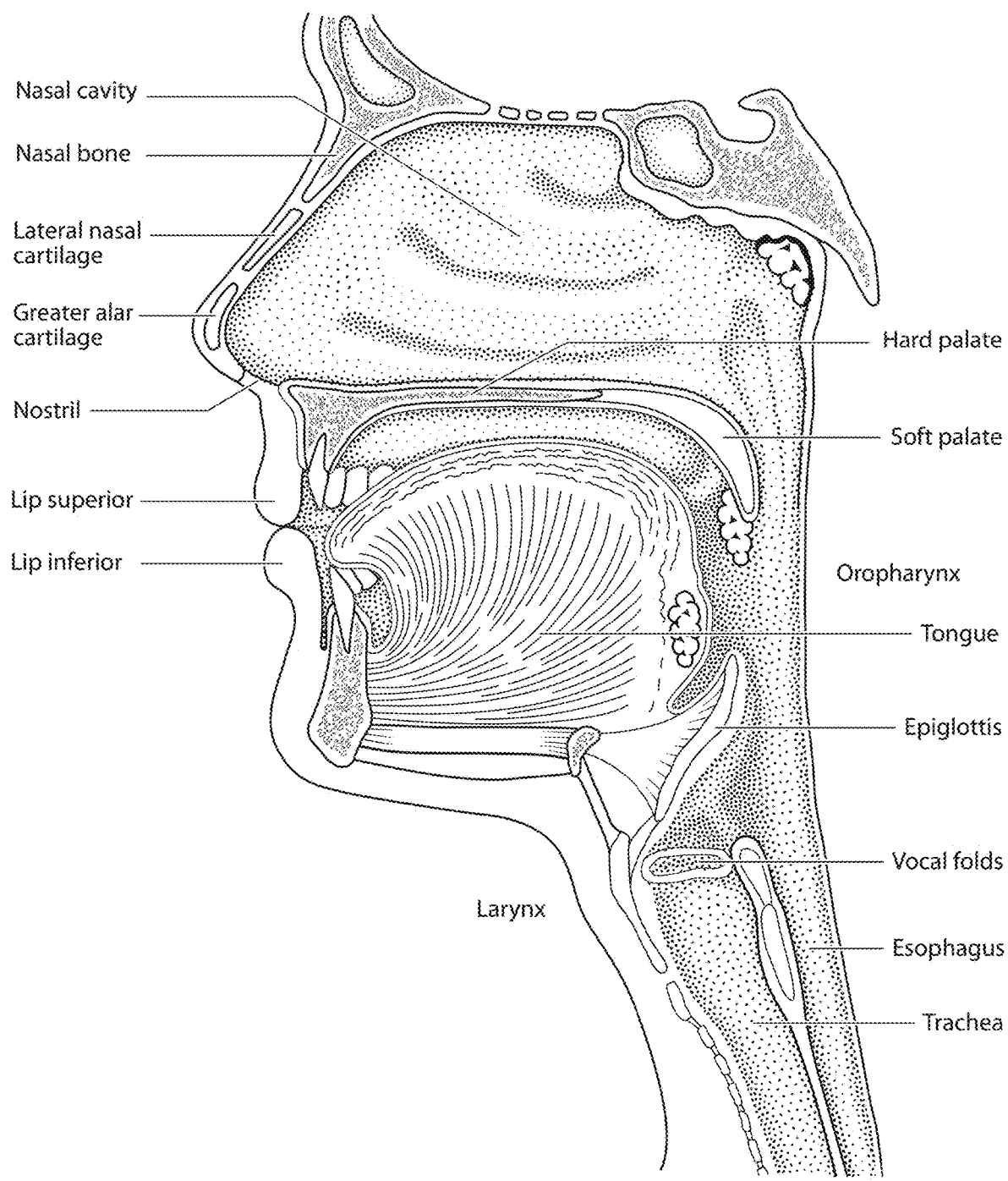

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
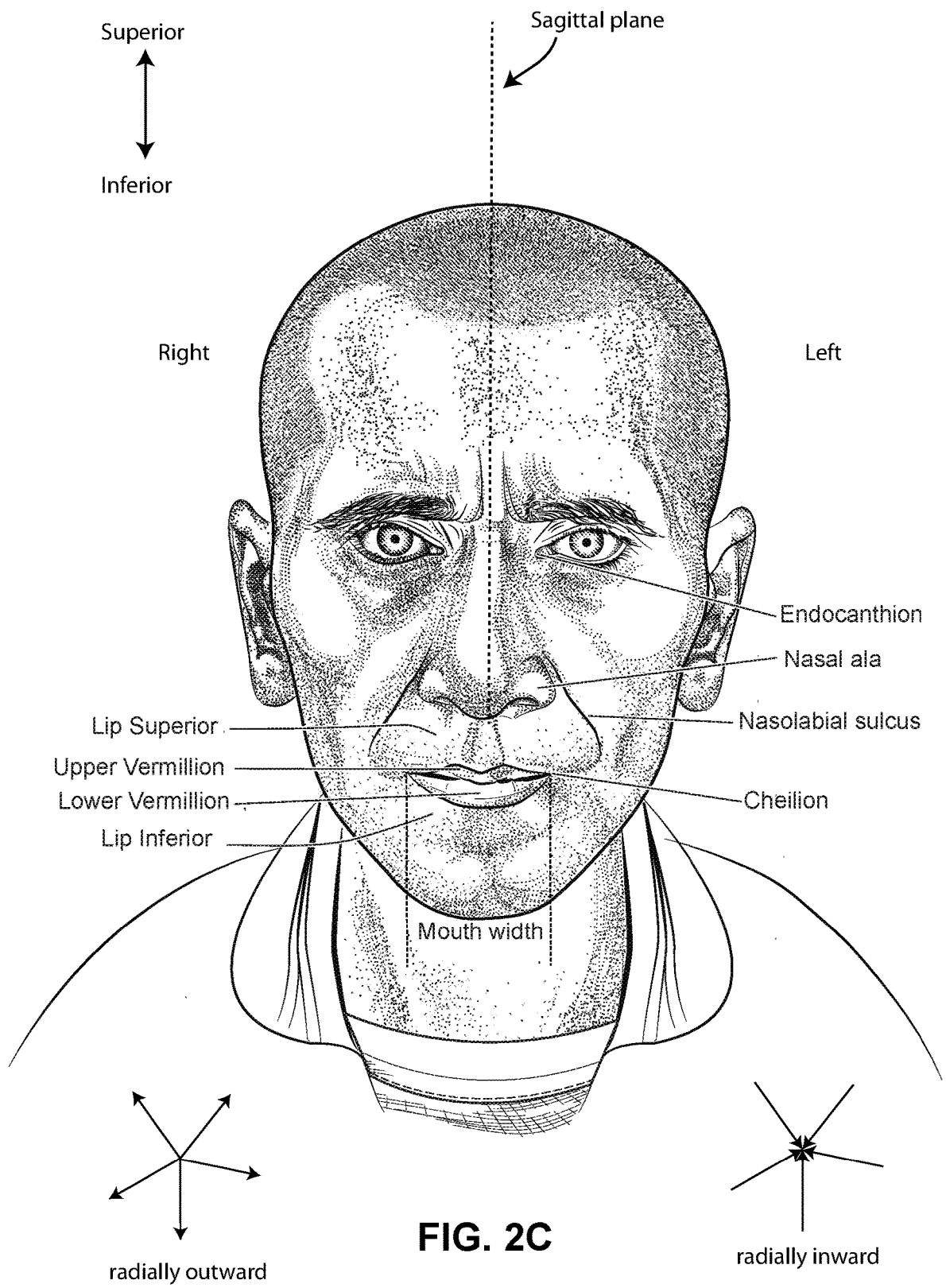

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
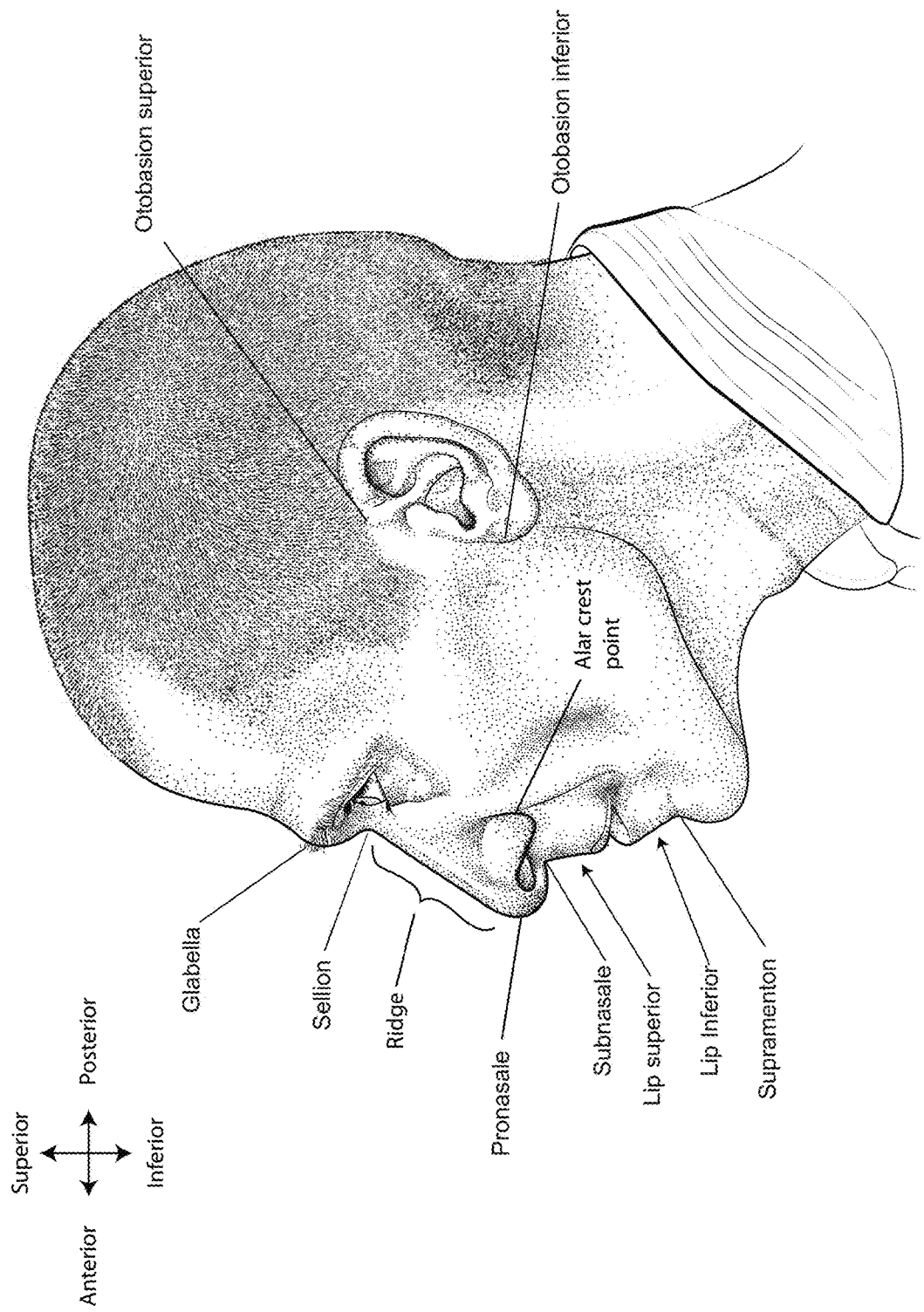

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
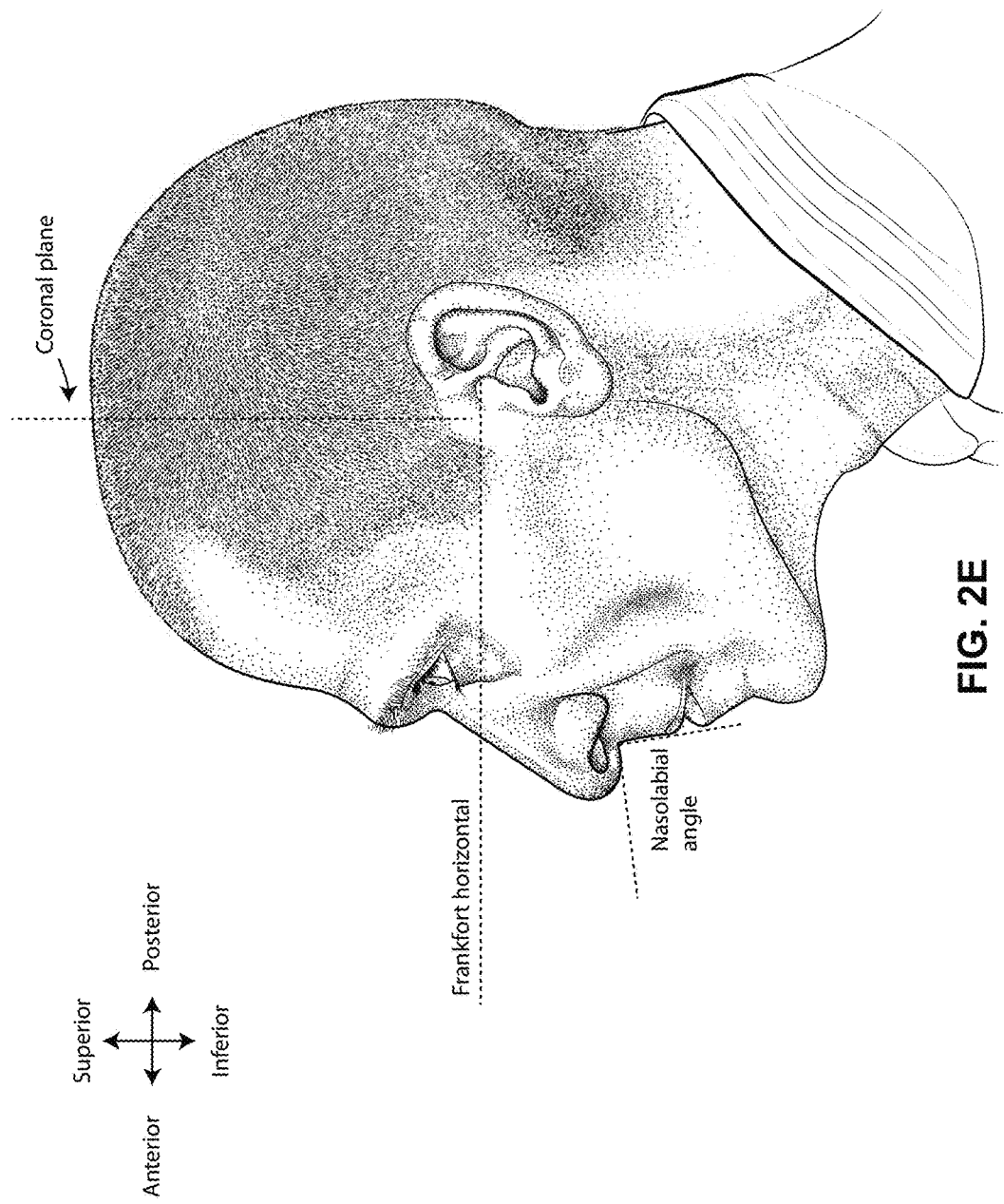

FIG. 2E is a further side view of a head. The approximate locations of the Frankfort horizontal and nasolabial angle are indicated. The coronal plane is also indicated.

Figure 2F:
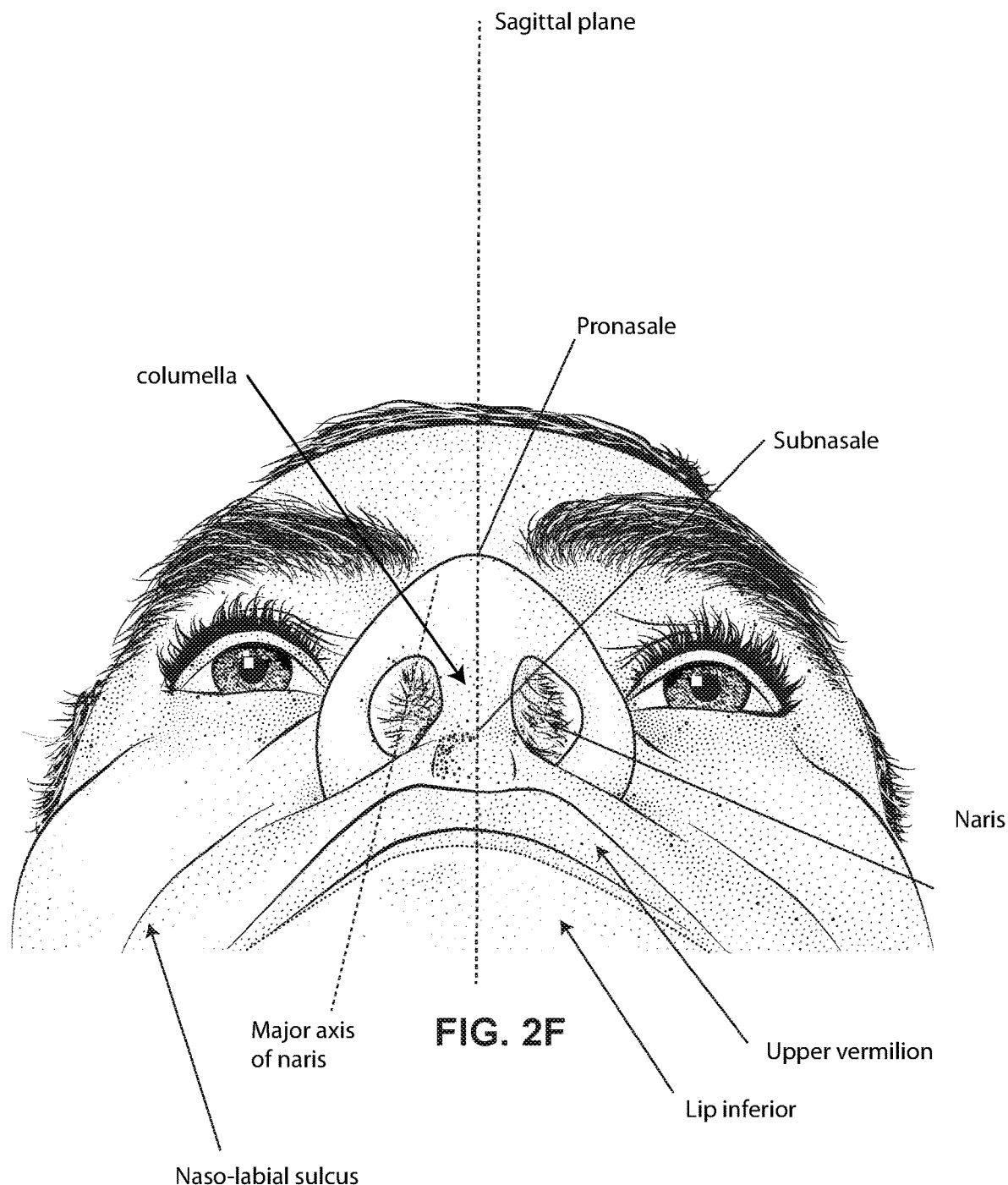

FIG. 2F shows a base view of a nose with several features identified including naso-labial sulcus, lip inferior, upper Vermilion, naris, subnasale, columella, pronasale, the major axis of a naris and the sagittal plane.

Figure 2I:
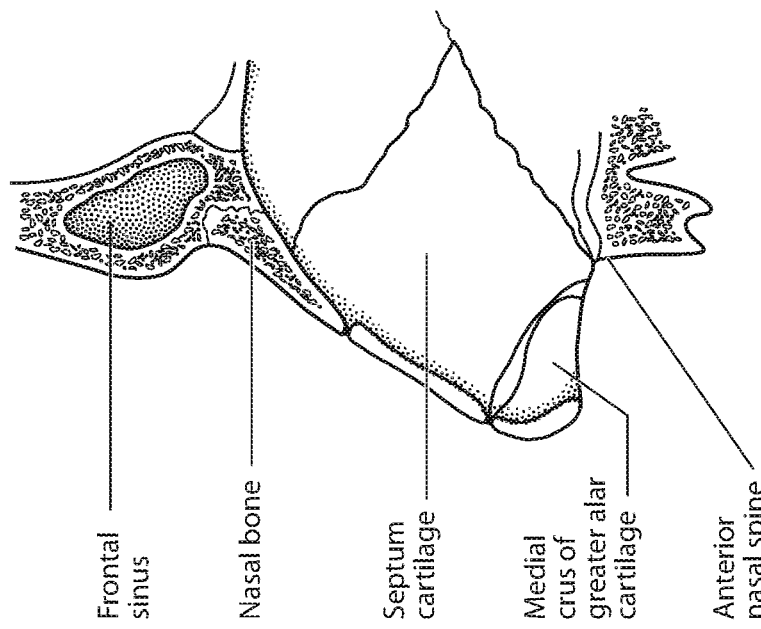
Figure 2H:
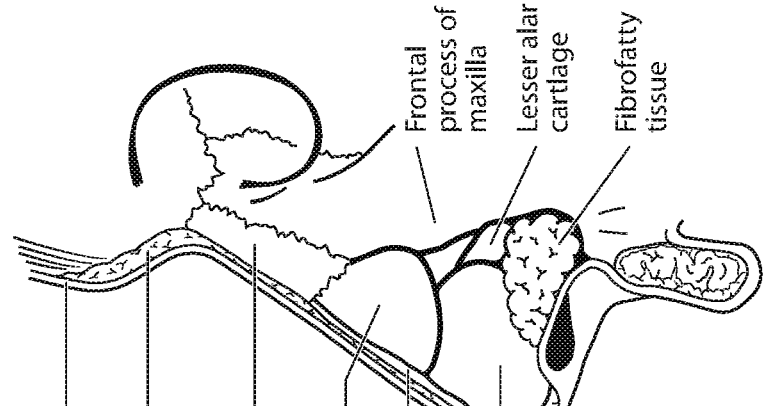
Figure 2G:

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

Figure 2J:
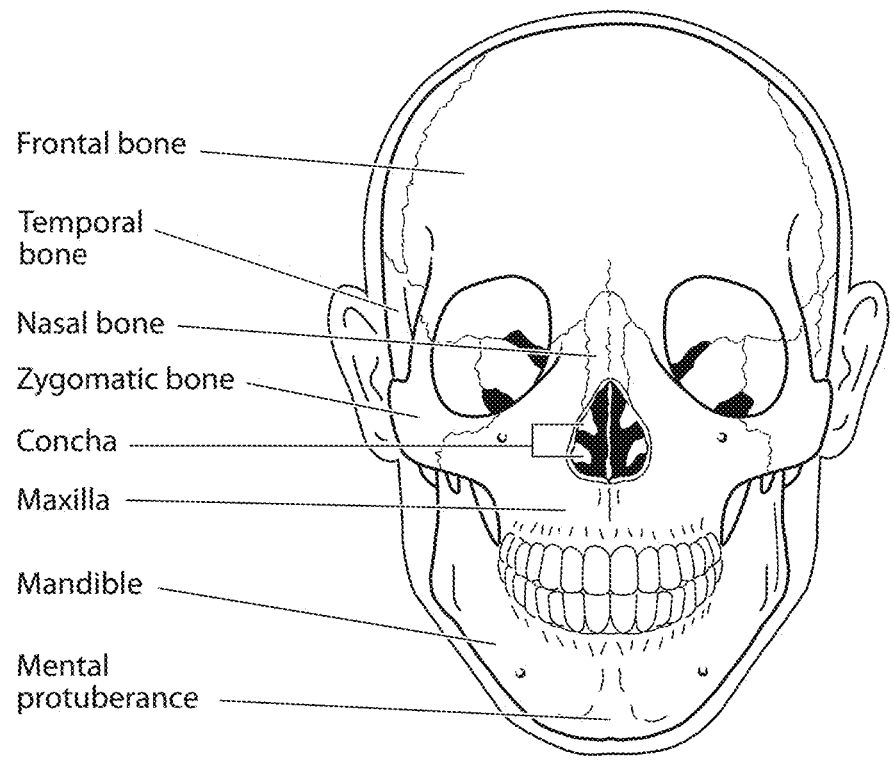

FIG. 2J shows a front view of the bones of a skull including the frontal, nasal and zygomatic bones. Nasal concha are indicated, as are the maxilla, and mandible.

Figure 2K:
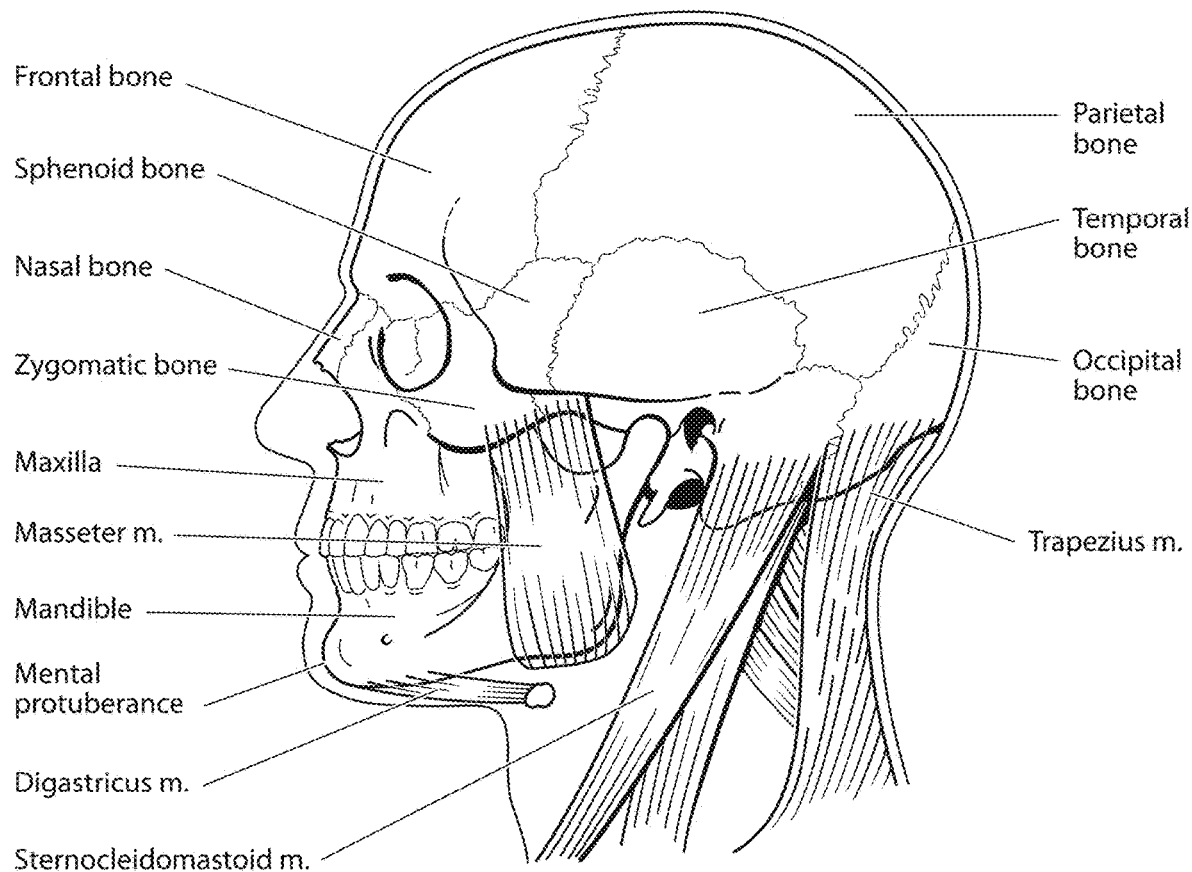

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
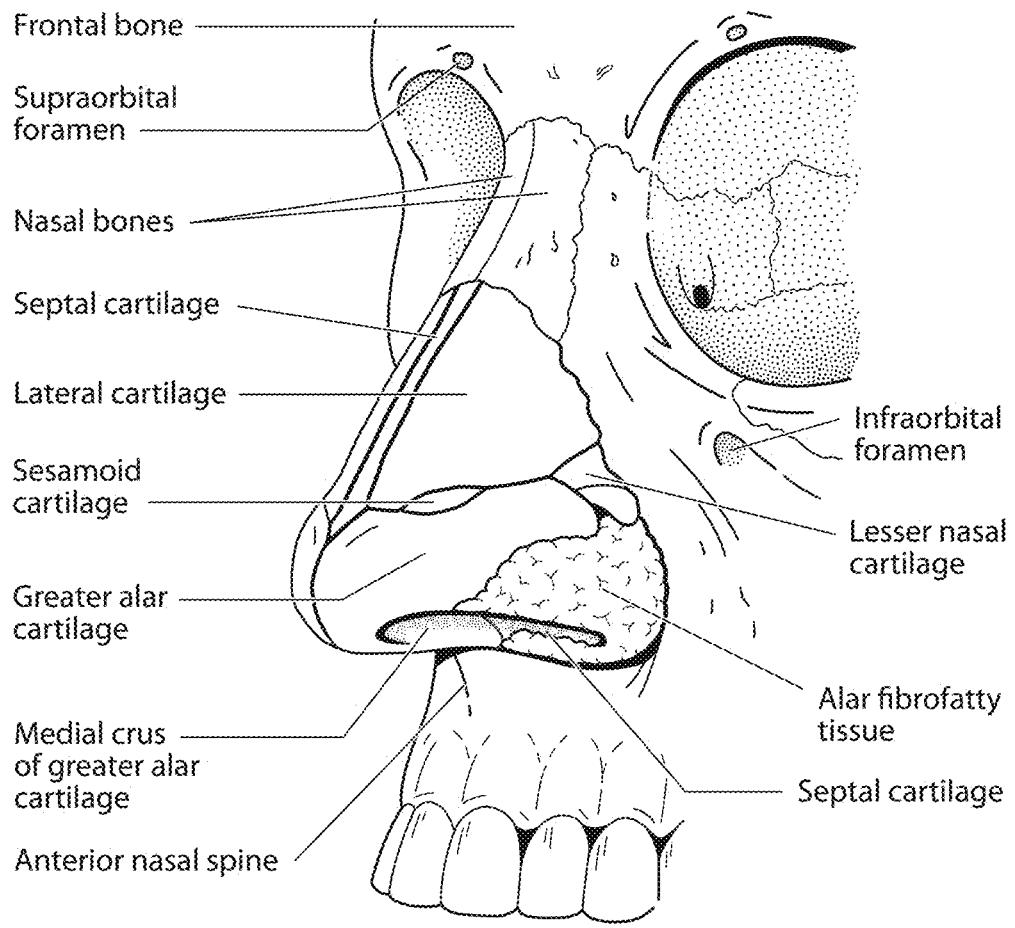

FIG. 2L shows an anterolateral view of a nose.

3.3 Patient Interface

Figure 3A:
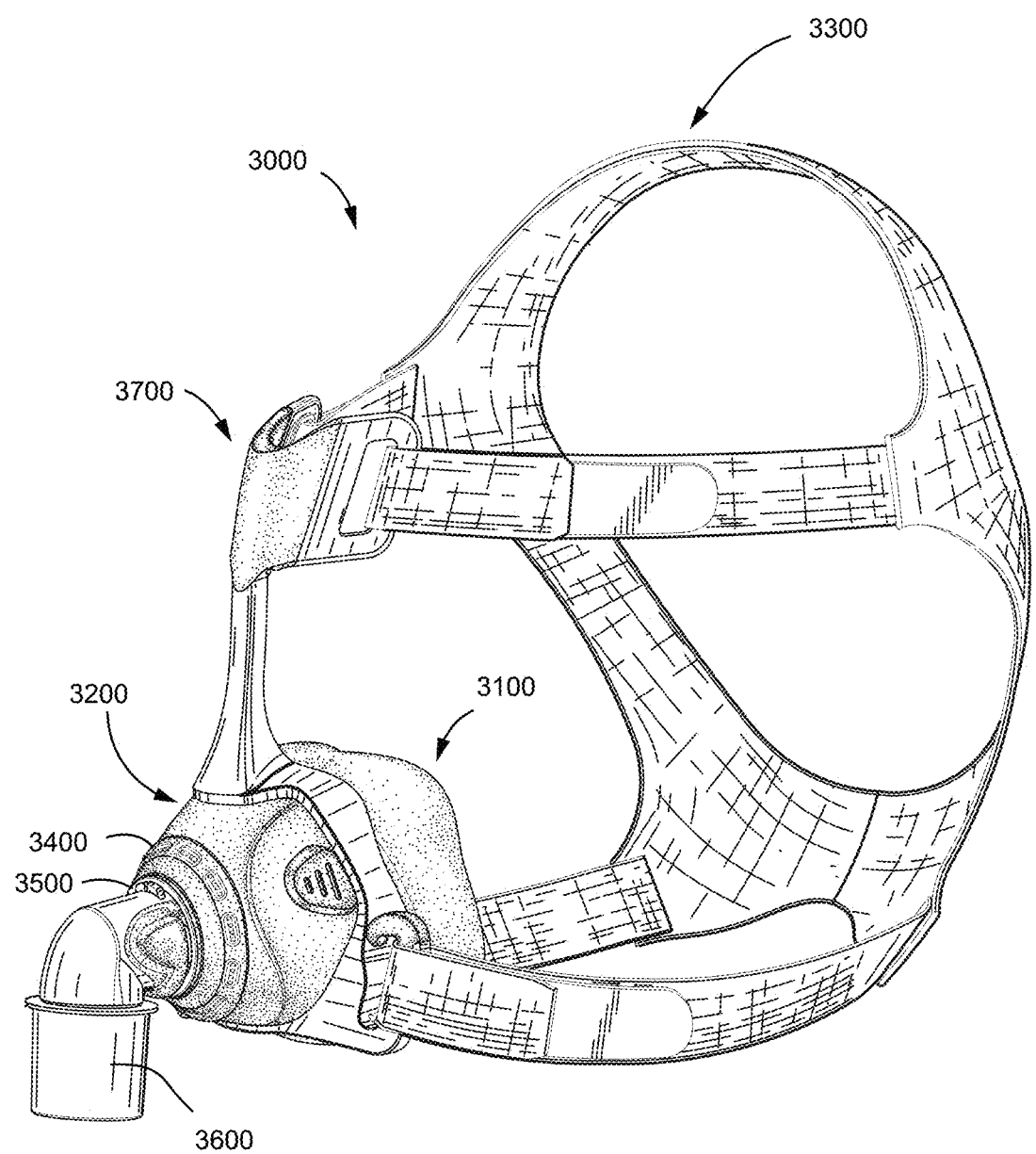

FIG. 3A shows a patient interface in the form of a nasal mask in accordance with one form of the present technology.

Figure 3B:
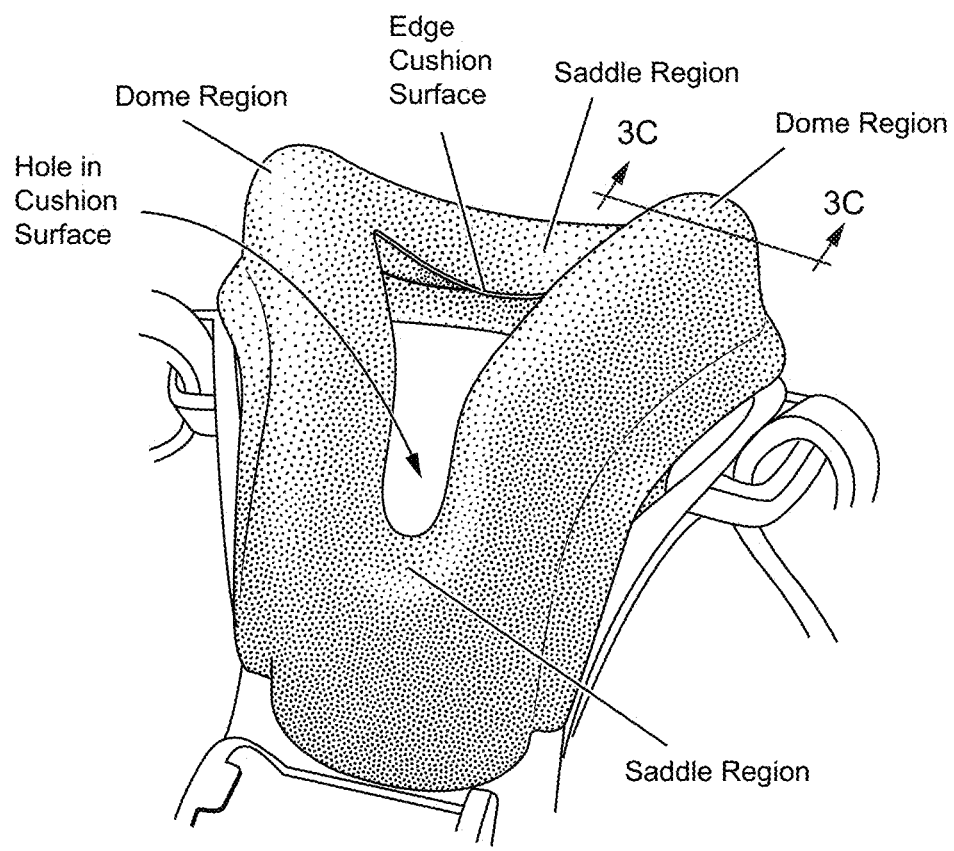

FIG. 3B shows a patient interface in the form of a full-face mask and depicting various contoured regions of a seal-forming structure, e.g., dome regions, saddle regions, edge cushion surface, and a hole in the cushion surface.

Figure 3C:
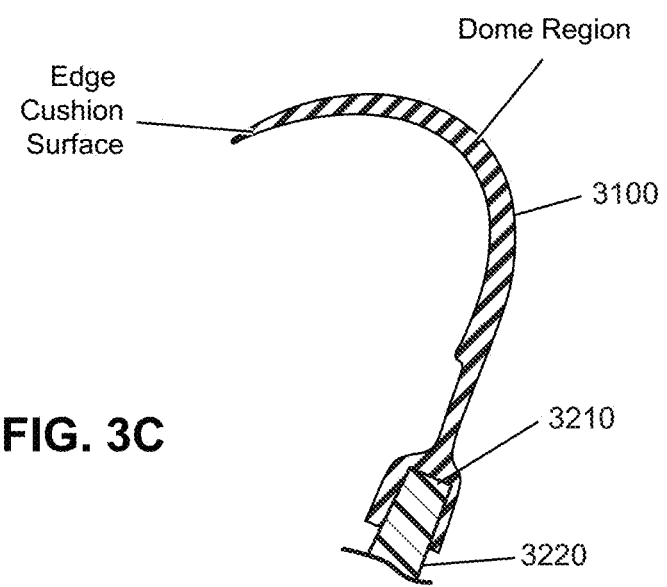

FIG. 3C is a cross-sectional view taken through line 3C-3C of FIG. 3B and showing an exemplary profile of the contour of the seal-forming structure.

Figure 3D:
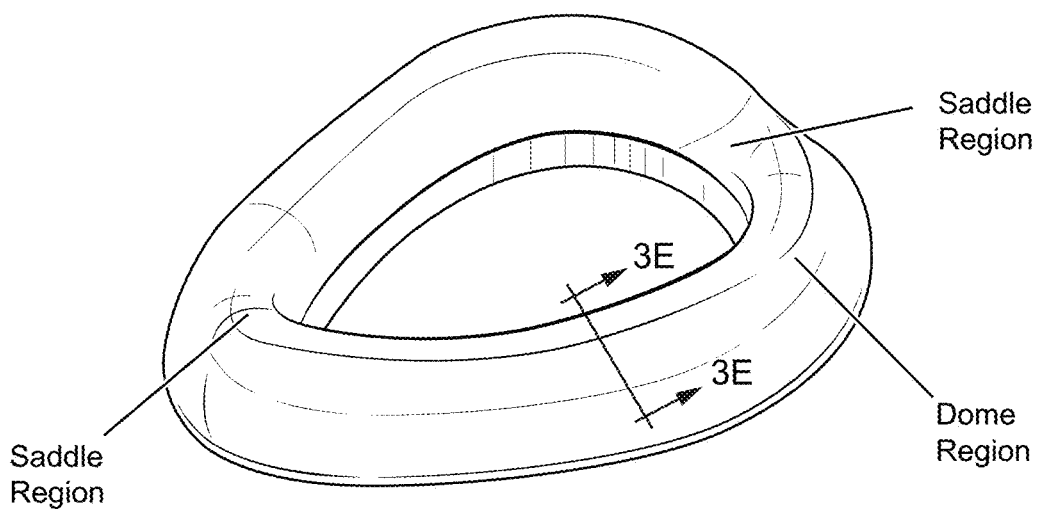

FIG. 3D shows a bladder cushion for a full-face mask, the bladder cushion having a torus shape, and depicting saddle regions and dome regions.

Figure 3E:
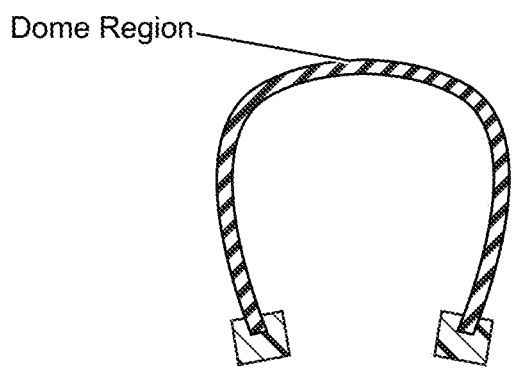

FIG. 3E is a cross-sectional view taken through line 3E-3E of FIG. 3D and showing an exemplary profile of the contour of the bladder cushion.

Figure 3F:
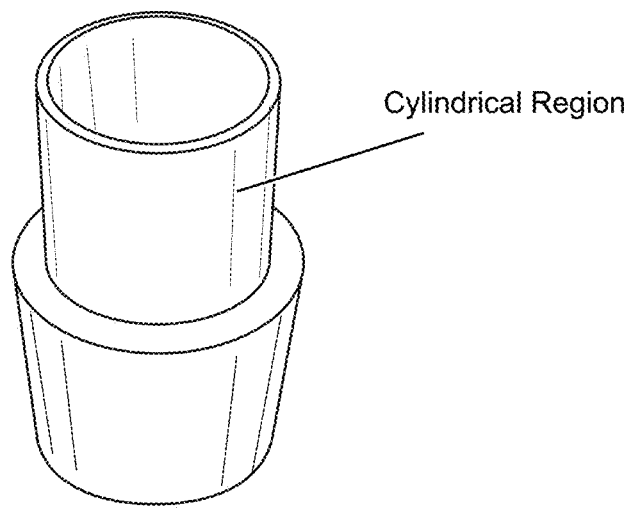

FIG. 3F depicts a swivel in accordance with one form of the present technology and an associated cylindrical region.

Figure 3G:
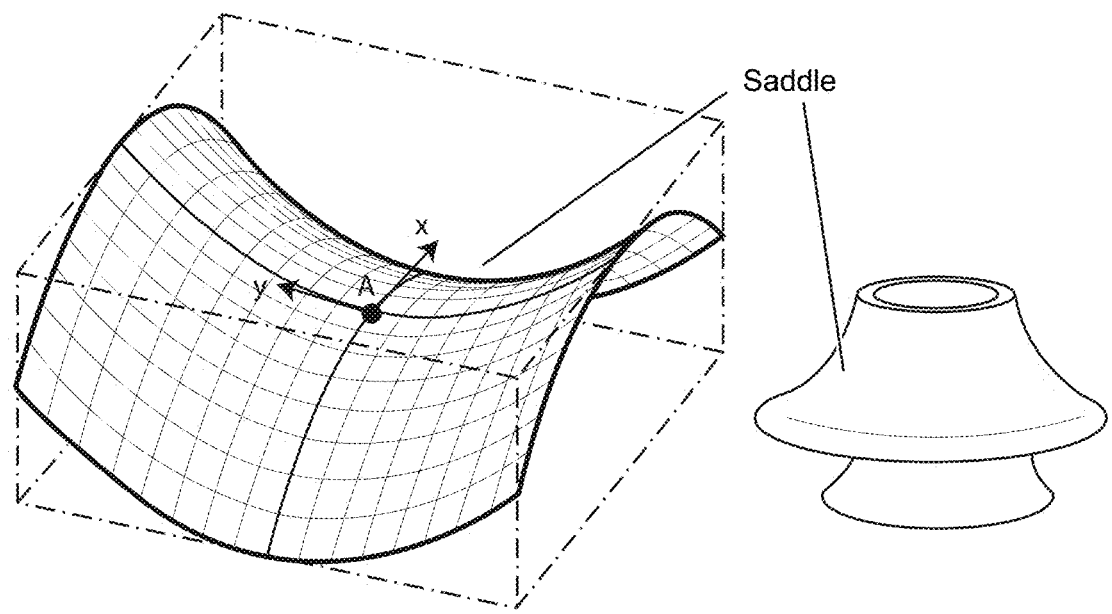

FIG. 3G depicts examples of a saddle region.

Figure 3H:
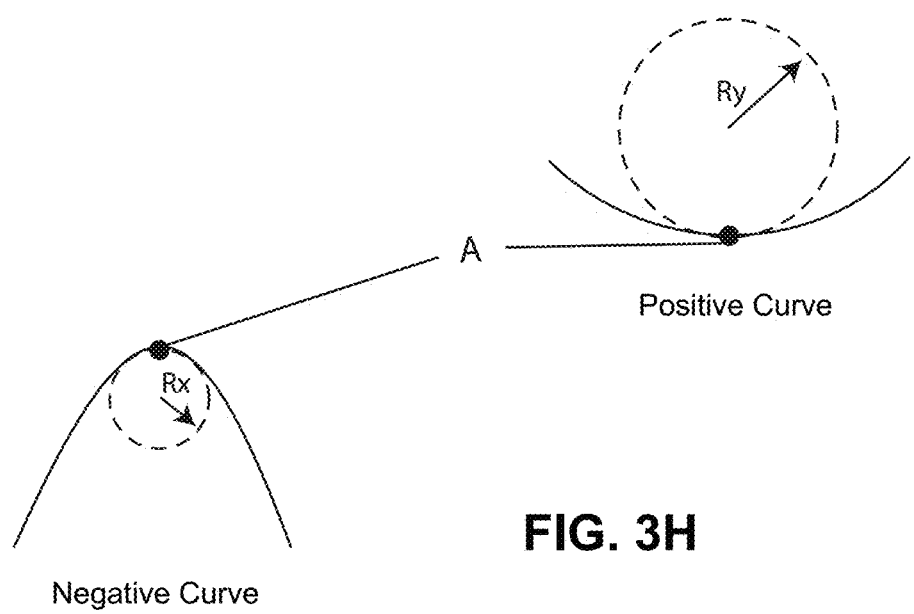

FIG. 3H depicts examples of a negative curve and a positive curve that combine to form the contour of a saddle region.

Figure 3I:
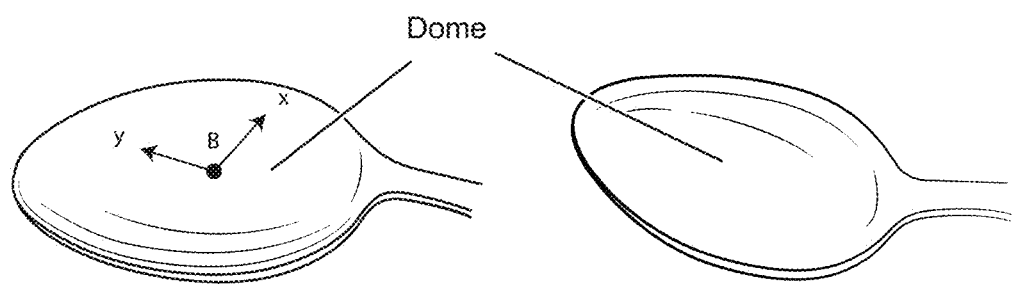

FIG. 3I depicts examples of a dome region.

Figure 3J:
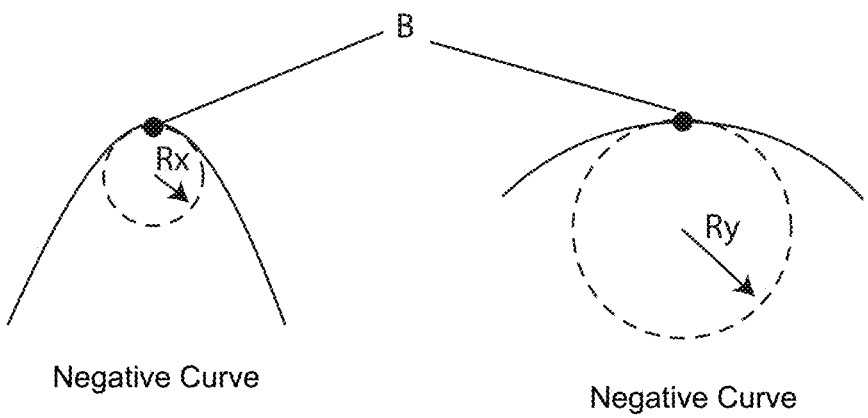

FIG. 3J depicts examples of the negative curves that combine to form the contour of a dome region.

Figure 4:
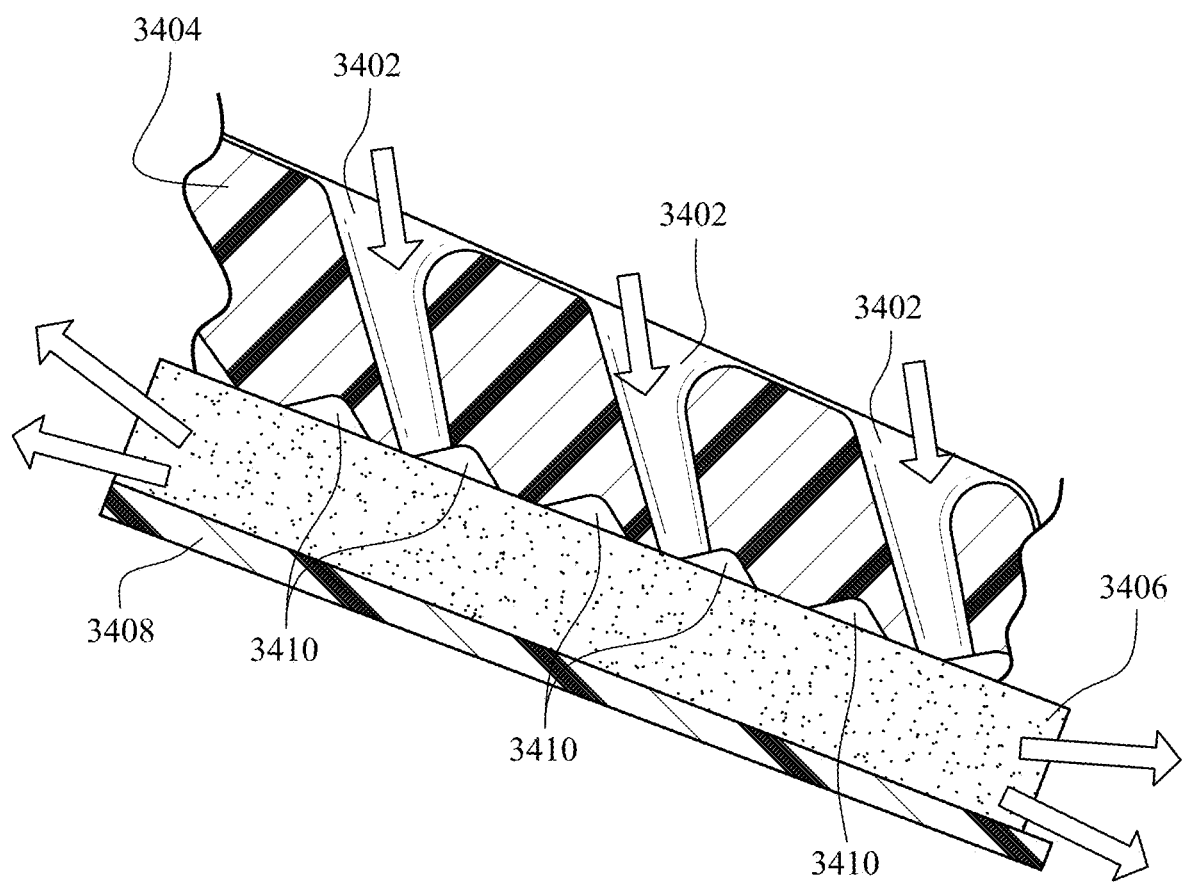

FIG. 4 depicts orifices, a diffusing member and a blocking member that form part of a gas washout vent.

Figure 5:
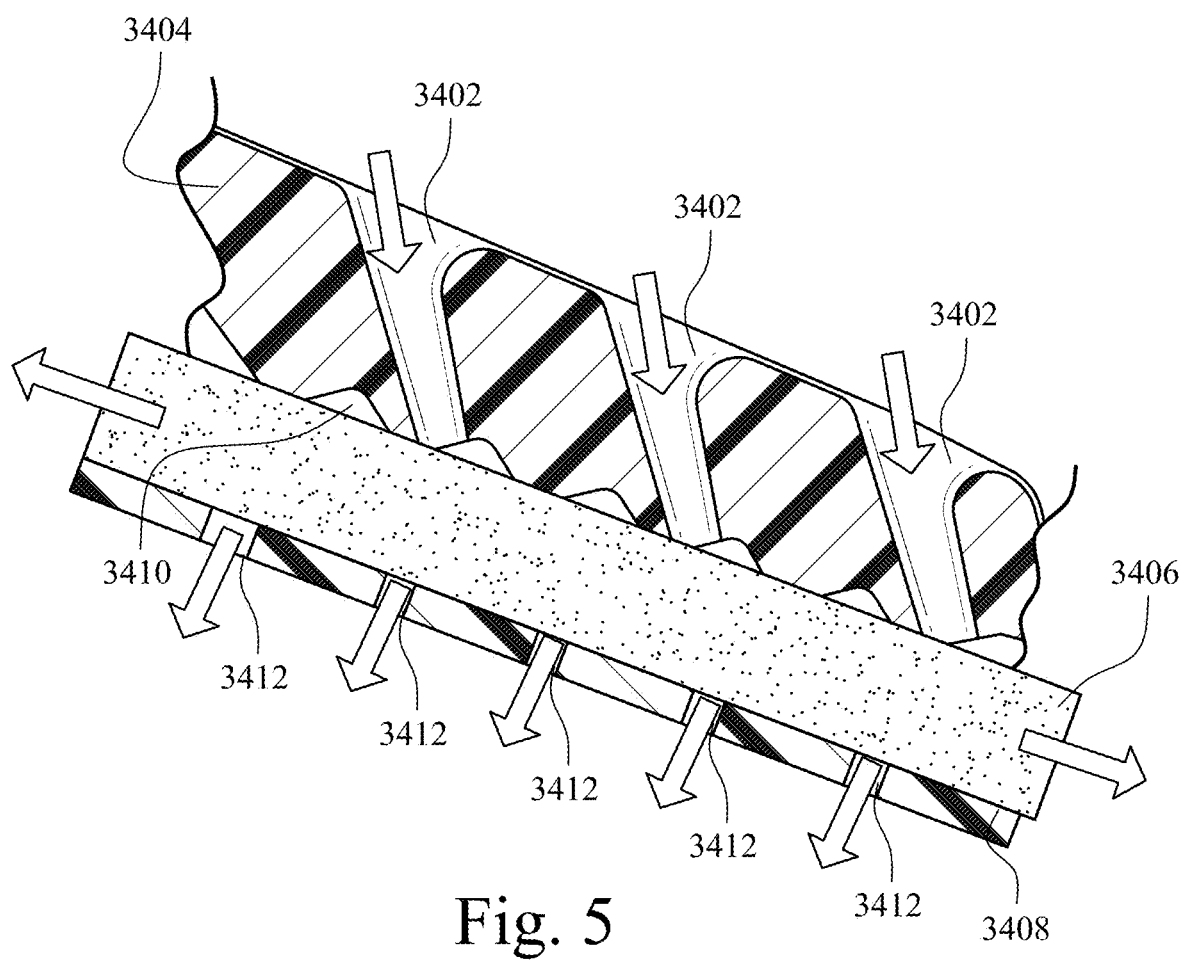

FIG. 5 depicts orifices, a diffusing member and a blocking member that form part of a gas washout vent where holes are provided in the blocking member.

Figure 6:
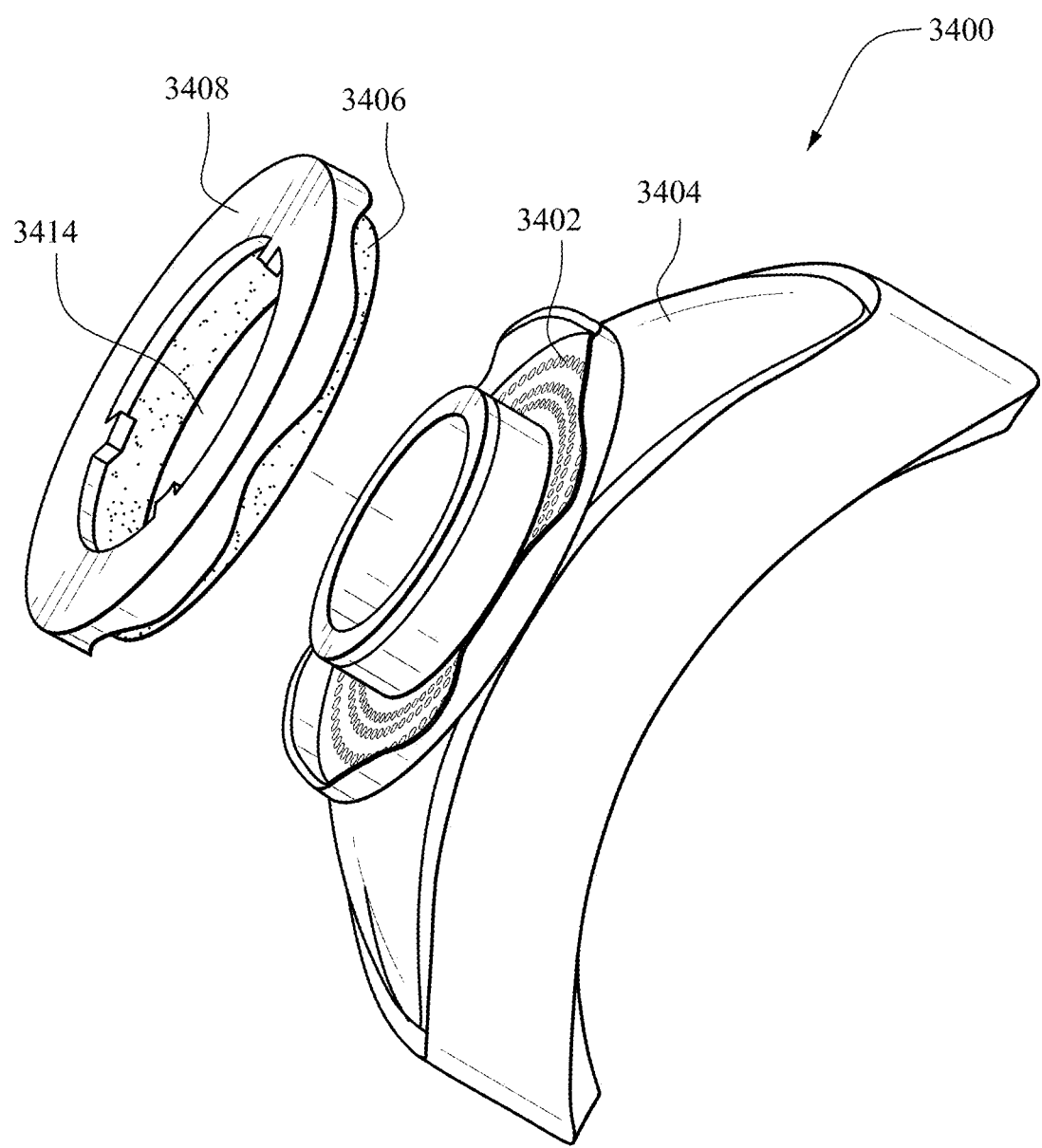

FIG. 6 depicts an exploded view of orifices, a diffusing member and a blocking member that form part of a gas washout vent formed circularly about a central hole.

Figure 7:
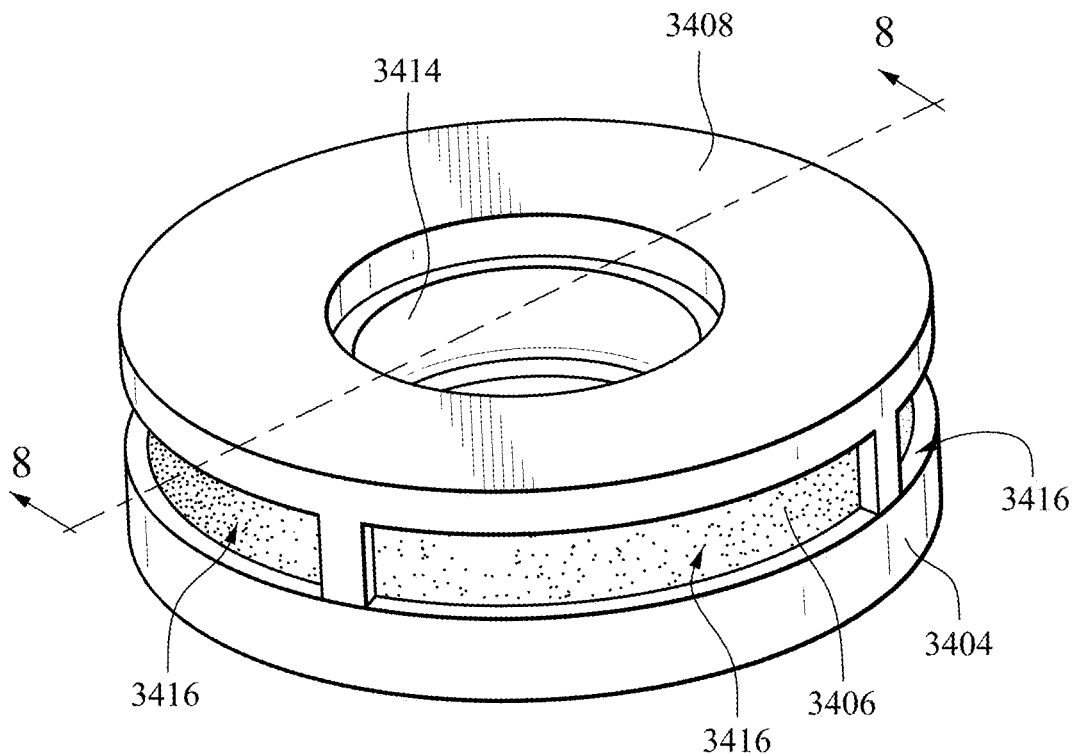

FIG. 7 depicts a simplified view of orifices, a diffusing member and a blocking member that form part of a gas washout vent formed circularly about a central hole.

Figure 8:
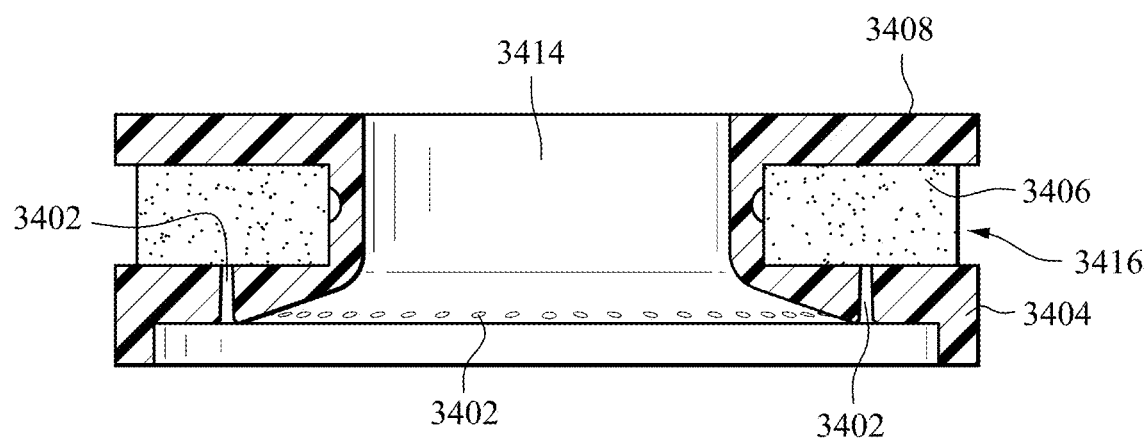

FIG. 8 depicts a cross-sectional view taken through line 8-8 of FIG. 7.

Figure 9A:
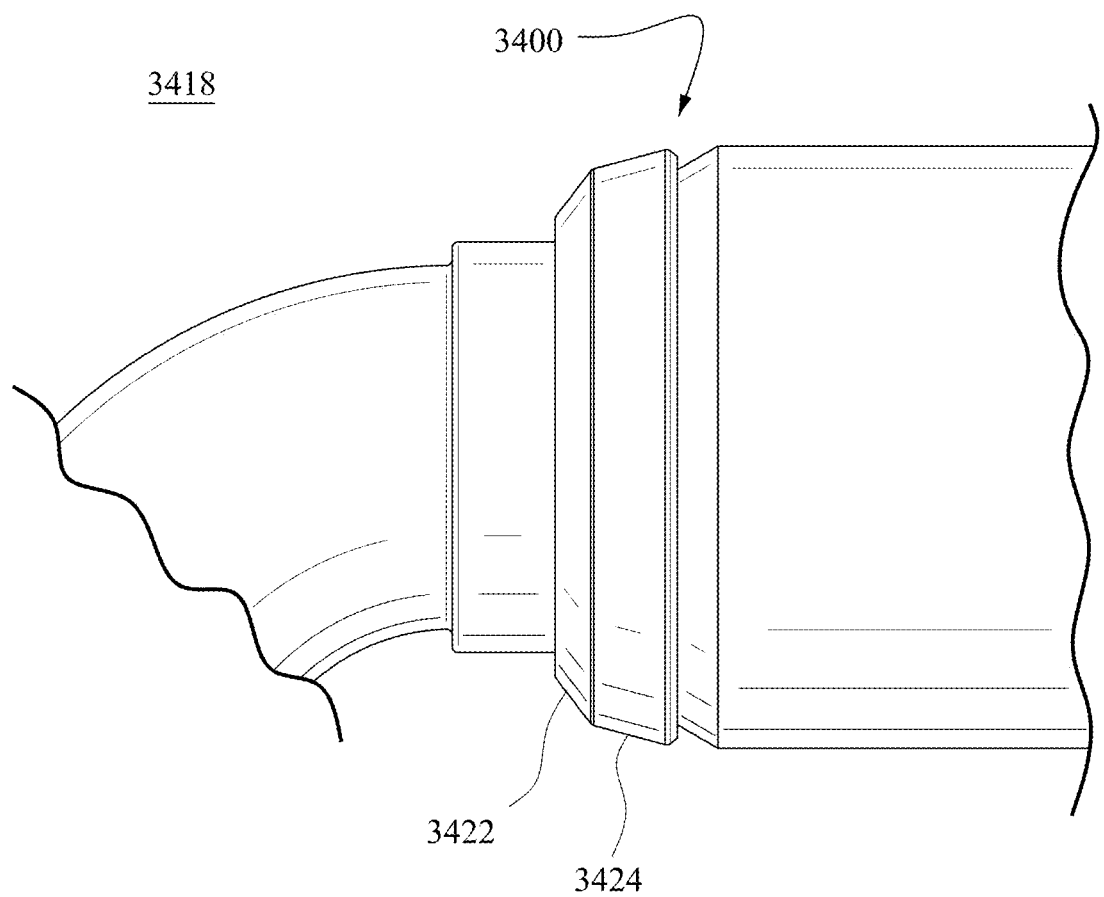

FIG. 9A depicts a partial view of an elbow with a gas washout vent with one annular outlet.

Figure 9B:
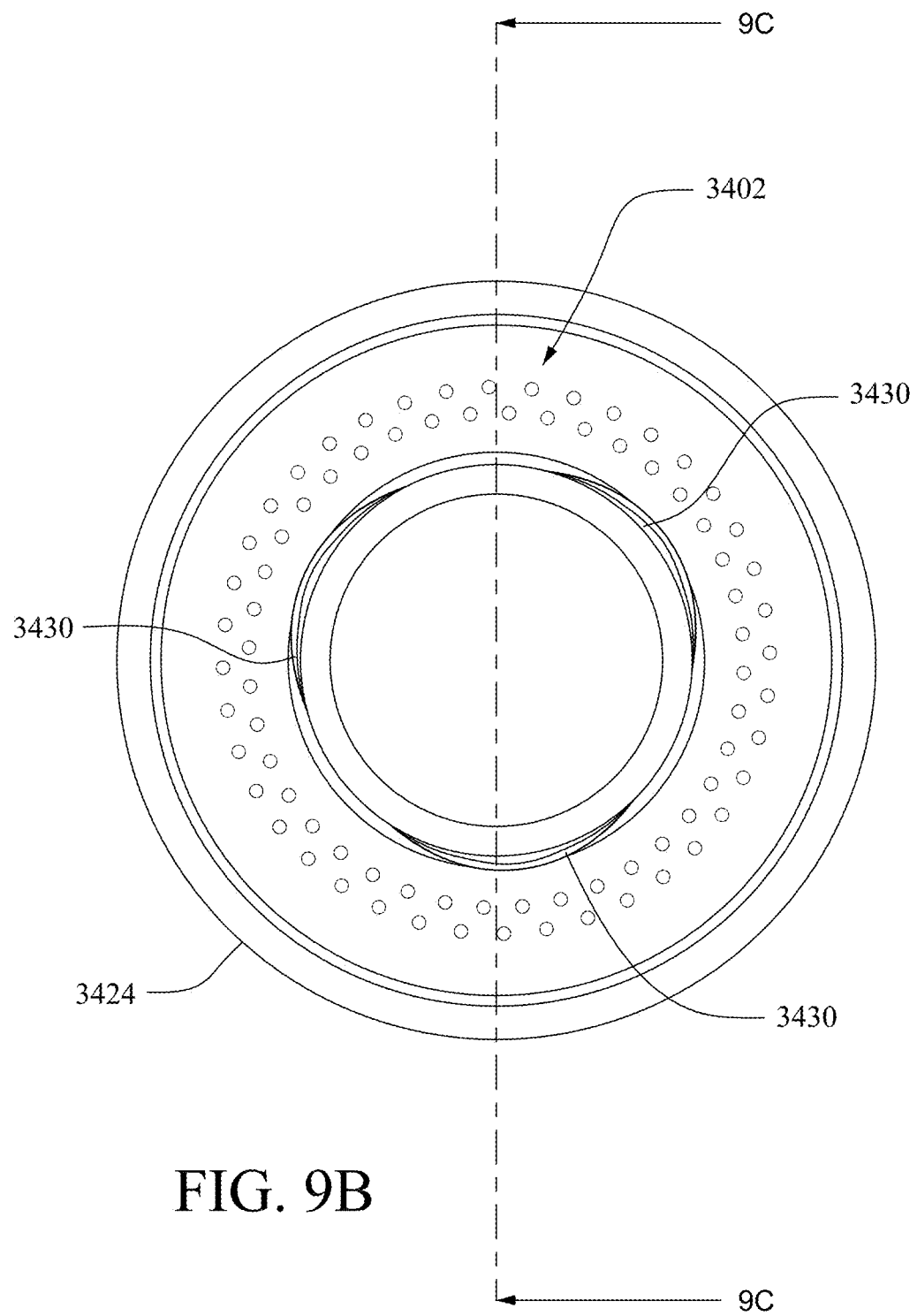

FIG. 9B depicts an axial view of orifices in the gas washout vent of FIG. 9B.

Figure 9C:
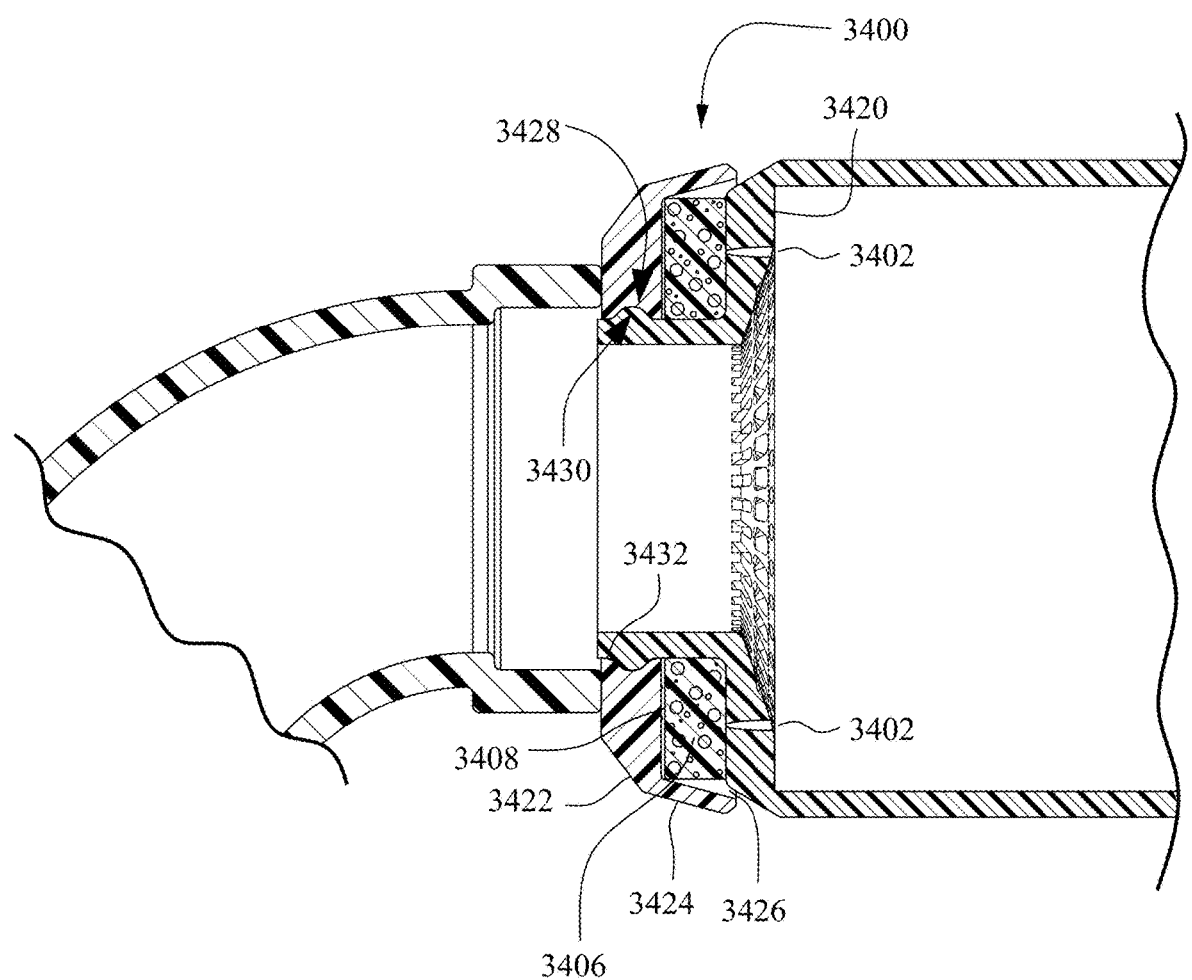

FIG. 9C depicts a cross-sectional view taken through the plane of the drawing of FIG. 9B, which is equivalent to the plane labelled 9C-9C in FIG. 9B.

Figure 10A:
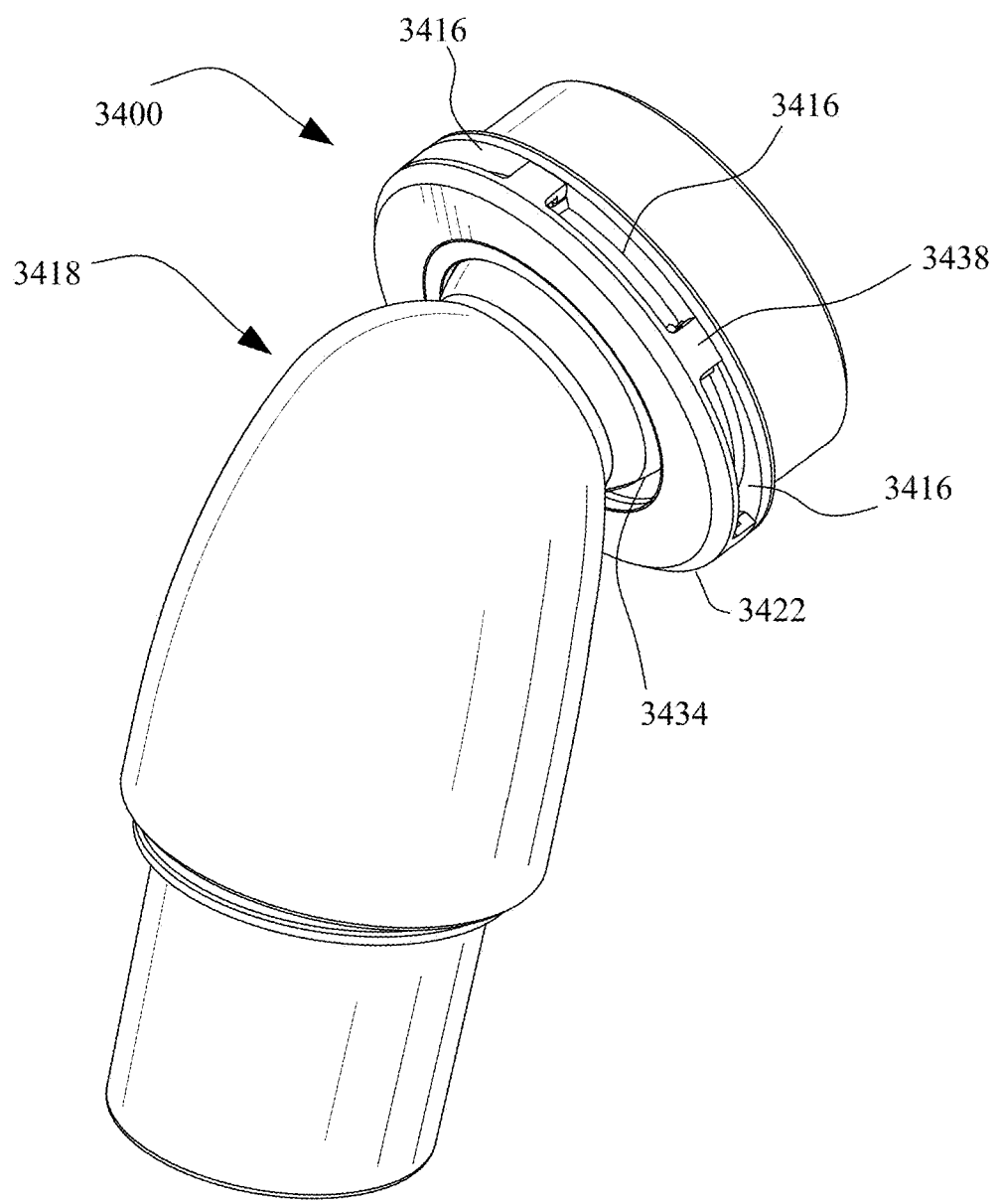

FIG. 10A depicts an elbow with a ball and socket joint and gas washout vent.

Figure 10B:
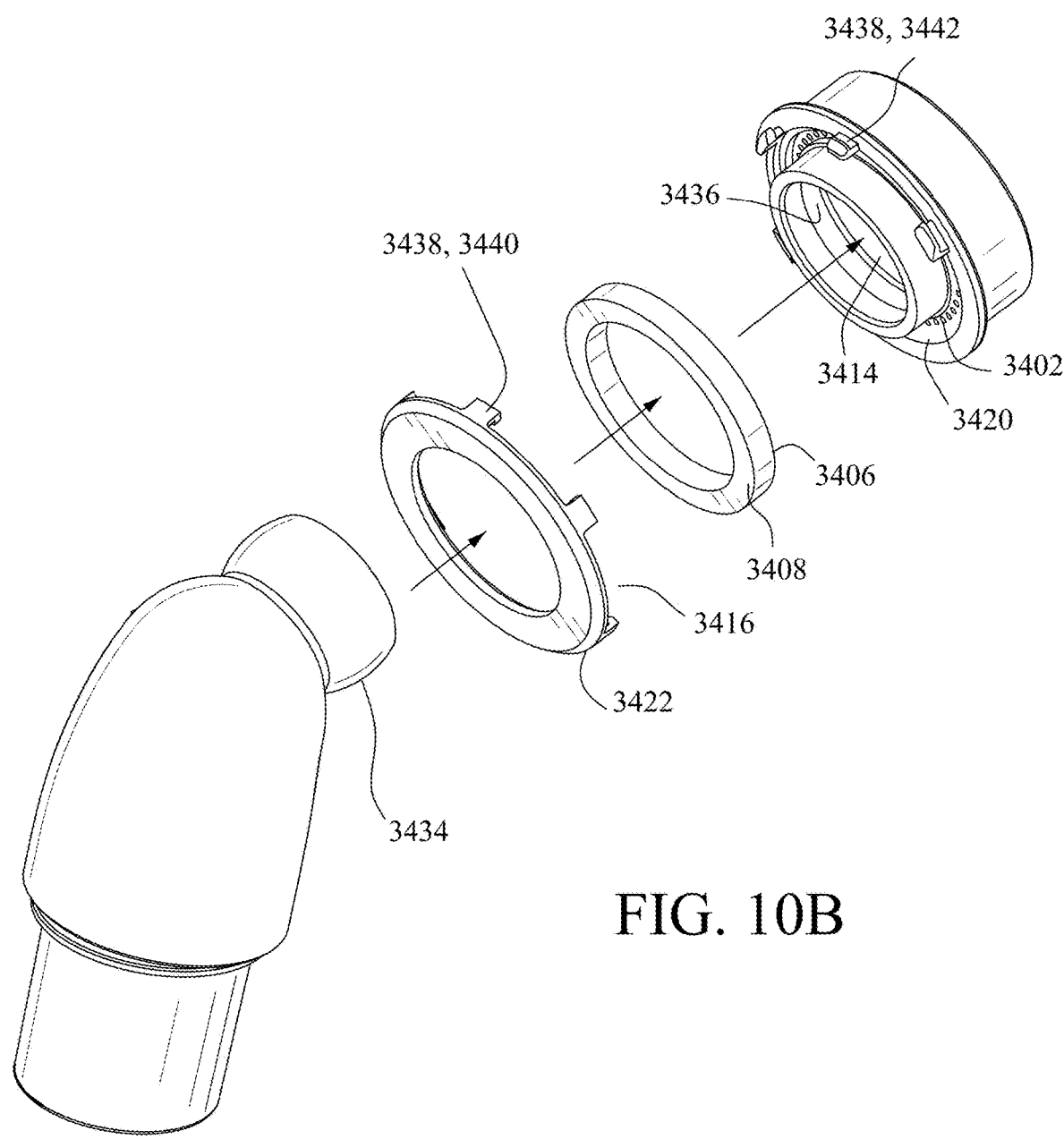

FIG. 10B depicts an exploded view of the elbow of FIG. 10A.

Figure 10C:
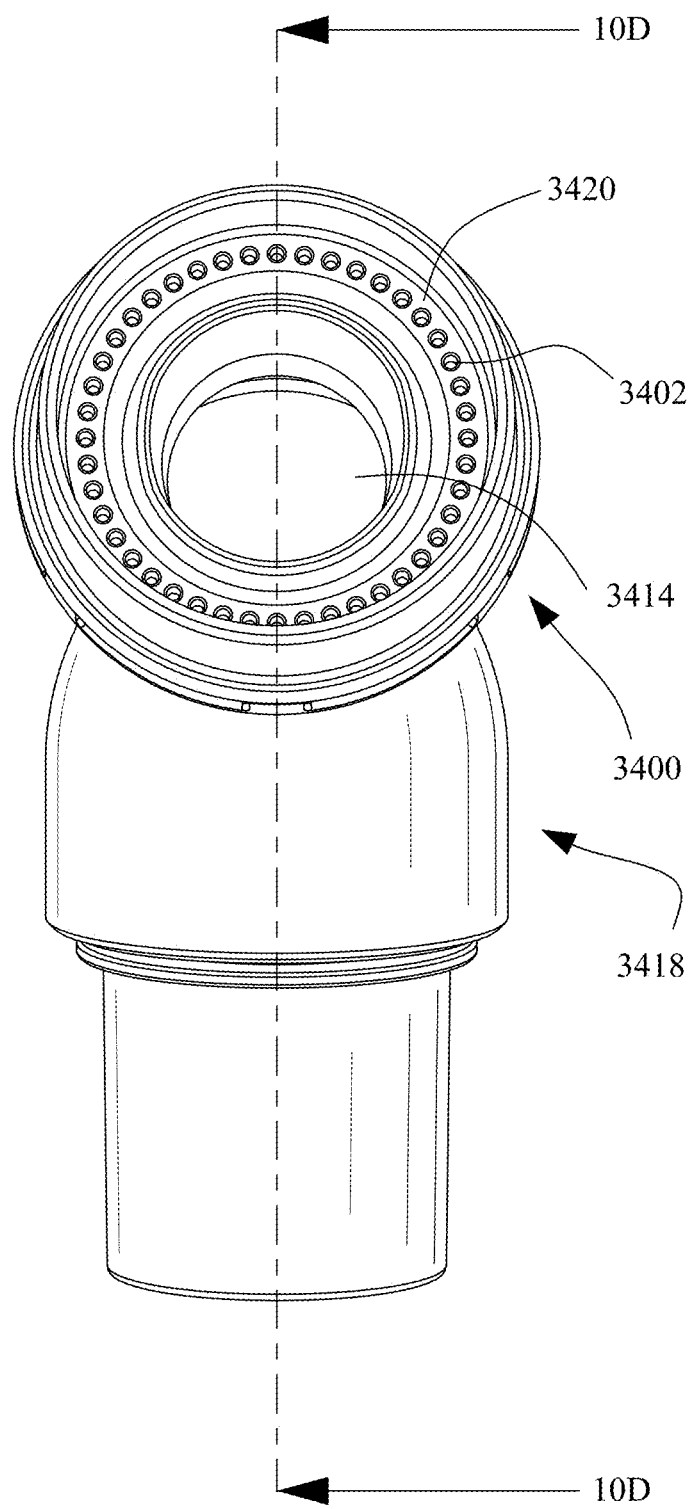

FIG. 10C depicts a side view of the elbow.

Figure 10D:
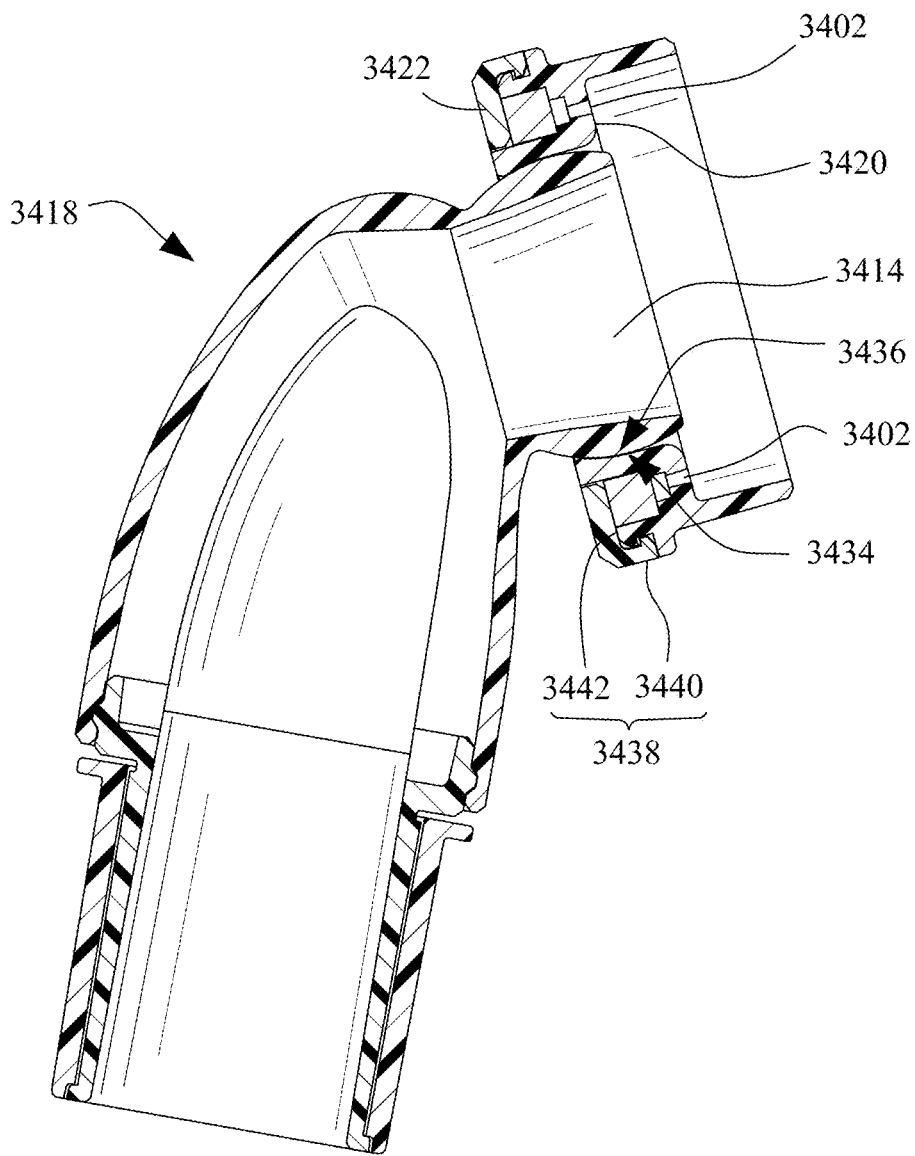

FIG. 10D depicts a cross-sectional view taking through line 10D-10D of FIG. 10C.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

4.3 Patient Interface

A non-invasive patient interface 3000 in accordance with one aspect of the present technology comprises the following functional aspects: a seal-forming structure 3100, a plenum chamber 3200, a positioning and stabilising structure 3300 and one form of connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

4.3.1 Seal-Forming Structure

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

4.3.2 Plenum Chamber

The plenum chamber 3200 has a perimeter 3210 (see FIG. 3C) that is shaped to be complementary to the surface contour of the face of an average person in the region where a seal will form in use. In use, a marginal edge 3220 (see FIG. 3C) of the plenum chamber 3200 is positioned in close proximity to an adjacent surface of the face. Actual contact with the face is provided by the seal-forming structure 3100. The seal-forming structure 3100 may extend in use about the entire perimeter 3210 of the plenum chamber 3200.

4.3.3 Positioning and Stabilising Structure 3300

The seal-forming portion 3100 of the patient interface 3000 of the present technology may be held in sealing position in use by the positioning and stabilising structure 3300.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

4.3.4 Vent

In one form, the patient interface 3000 includes a vent 3400 constructed and arranged to allow for the washout of exhaled carbon dioxide and thus may also be referred to as a gas washout vent.

One form of vent 3400 in accordance with the present technology comprises a plurality of orifices 3402, for example, about 20 to about 80 orifices, or about 40 to about 60 orifices, or about 45 to about 55 orifices, inclusive of each whole integer with the stated ranges.

The vent 3400 may be located in the plenum chamber 3200. Alternatively, the vent 3400 is located in a decoupling structure 3500, e.g., a swivel (see FIG. 3A).

FIG. 4 illustrates a cross-section through some of the orifices 3402. The orifices 3402 are illustrated as holes through a wall 3404 of the plenum chamber 3200. However, the orifices 3402 may be located in locations other than the wall 3404. For example, the orifices 3402 may be located between the decoupling structure 3500 and the connection port 3600 or in a portion of the air circuit 4170, preferably near the connection port 3600. The holes are illustrated with a diameter that is smaller than an axial length of the hole. The length and/or diameter may be chosen so that an appropriate flow rate is generated when the plenum chamber 3200 is pressurized to the therapy pressure. The flow through the orifices 3402 may be choked (e.g. a Mach number of 1) at the therapy pressure (e.g. at 4 $cmH_2O$ or greater pressure) or the flow may generate less than sufficient pressure drop to be choked. A choked flow may result in substantially all of the pressure drop in the vent 3400 being caused by the orifices 3402. The arrows conceptually illustrate direction of flow when the plenum chamber 3200 is pressurized above ambient pressure.

The orifices 3402 are formed through a thickness of material of the wall 3404. Each of the orifices 3402 defines an axis, e.g., along a center of the orifice. The axis forms an acute angle with a normal to a surface of the wall 3404. The angle may be between 15 and 75 degrees or between 30 and 60 degrees, including any integer within the stated ranges. For example, the angle may be about 45 degrees.

The orifices 3402 are covered by a diffusing member 3406 so that flow exiting the orifices 3402 impinges on and flows at least partially into the diffusing member 3406. The diffusing member 3406 may be formed from a material, such as a porous material, that allows gas to flow through the material but diffuses any jet or other flow formation exiting the orifices 3402. Some suitable examples of diffusing material include a non-woven fibrous material; a woven fibrous material; or an open cell foam material. The diffusing material may be similar to or the same as a filter media. The diffusing member 3406 may reduce perceptible noise generated by the vent 3400 in use (e.g., when therapy pressure is applied).

The diffusing member 3406 is illustrated as covered by a blocking member 3408 that prevents gas from flowing out of the orifices 3402 and directly through the diffusing member 3406. The blocking member 3408 may be constructed, at least in part, from an air-impermeable material. The air-impermeable material may be any suitable flexible or rigid material. For example, the air-impermeable material may be a rigid plastic (e.g., molded polycarbonate) or a flexible plastic (e.g., a plastic commercially available in sheet form). The blocking member 3408 may be formed integrally with the diffusing member 3406, formed separately but permanently affixed to the diffusing member 3406, formed separately and in removable contact with the diffusing member 3406, or combinations thereof. The blocking member 3408 is illustrated as opposite the outlet orifices 3402 with respect to a thickness of the diffusing member 3406.

The blocking member may cause the flow to change direction (with respect to the direction through the orifices 3402) before exiting the diffusing member 3406. The blocking member 3408 and/or diffusing member 3406 may be configured so that flow out of the orifices 3402 must flow at least a predetermined distance through the diffusing member 3406 prior to exiting to ambient atmosphere. The blocking member 3408 may also be configured to provide a particular direction and/or orientation for flow exiting the vent 3400 to minimize any disturbance to the wearer and/or bed partner caused by the flow. For example, the blocking member 3408 may cause gas to flow through the diffusing member 3406 and generally parallel to a surface of blocking member 3408 nearest to the diffusing member 3406.

In FIG. 4, the orifices 3402 and the diffusing member 3406 are oriented relative to one another such that a central axis of each of the orifices is not perpendicular to a nearest surface of the diffusing member 3406, although a perpendicular arrangement could also be provided as illustrated in FIG. 8.

Channels 3410 may also be provided on an outer surface of the wall 3404. The channels 3410 are illustrated with a V-shaped cross-section but could be formed with any suitable cross-section such as a U-shape. The channels 3410 may configured to allow liquid to drain away from one or more outlets of the orifices 3402. The orifices 3402 may formed in a leg of the V-shape or U-shape.

FIG. 5 illustrates an alternate configuration of the blocking member 3408. In FIG. 5, the blocking member 3408 includes holes 3412. The holes 3412 may direct the flow out of the diffusing member 3406 on the opposite side from the orifices 3402 but in a different direction. Thus the flow path is not straight through the orifices 3402 and the diffusing member 3406. Although the arrows associated with the holes 3412 are illustrated parallel, this is for ease of illustration only. The holes 3412 may be configured to redirect the flow in multiple directions.

The holes 3412 each define an axis that is neither aligned with nor parallel to an axis defined by each of the orifices 3402. When viewed in the cross-section of FIG. 5, any one axis defined by a hole 3412 and any one axis defined by an orifice 3402 forms an angle. The angle may be between 15 and 75 degrees or between 30 and 60 degrees, including any integer within the stated ranges. For example, the angle may be about 45 degrees.

FIGS. 6-8 illustrates an alternate configuration of the vent 3400. FIG. 6 illustrates a partially exploded view, FIG. 7 illustrates a simplified assembled view and FIG. 8 illustrates a cross-sectional view taken along line 8-8 of FIG. 7. In these figures, the orifices 3402 are illustrated in a circular array around a central hole 3414. The circular array is illustrated to include three circular rows of holes where the two inner-most circular rows are closer together than the outer-most circular row, but any number of circular rows may be provided an spacing between the rows may be equal. The central hole 3414 allows for fluid communication between the plenum chamber 3200 and the connection port 3600 and thus the air circuit 4170.

The diffusing member 3406 and the blocking member 3408 are also illustrated as being disposed around the central hole 3414. With this configuration, the blocking member 3408 may be removably attached (e.g., a removable snap fit or threaded engagement) or fixedly attached (e.g., permanent adhesive or a snap fit that must be broken to disassemble) and the diffusing member 3406 may be fixed to the blocking member 3408 or not fixed to but retained by the blocking member 3408. As best viewed in FIG. 7, radial openings 3416 are provided for gas to escape the diffusing member 3406 radially outward from the central hole 3414.

FIGS. 9A to 9C illustrate another alternate configuration of the vent 3400. FIG. 9A illustrates a partial view of a flow passage in the form of an elbow 3418, which may be disposed between a decoupling structure 3500 and connection port 3600 (both of which are illustrated in FIG. 3A), and includes a vent 3400. This configuration largely conceals the features of the vent 3400 and thus the remaining description is with respect to FIGS. 9B and 9C.

FIG. 9B illustrates an axial view with the cap 3422 and diffusing member 3406 omitted. This provides a clear view of the outlet orifices 3402. Two annular rows, each including forty of the outlet orifices 3402 are illustrated. The orifices are offset so that the outlet orifices 3402 in the inner row and the outer row are not radially aligned. This configuration may allow for annular rows to have closer radial spacing. Although two rows are illustrated, any number of rows may be provided, for example one row or three or more rows. Although forty outlet orifices 3402 are illustrated in each annular row, more or less may be provided as required to maintain appropriate levels of gas washout. For example, one, five, ten, fifteen, twenty, twenty five, thirty, thirty five, forty, forty five, fifty or more outlet orifices 3402, or any number in between, may be provided per annular row.

In FIG. 9C, the annular array of orifices 3402 are visible in the cross-section through a wall 3420. The wall 3420 is similar to wall 3404 except that the wall 3420 is illustrated remote from the plenum chamber 3200; however, the wall 3420 may be part of the plenum chamber 3200.

The diffusing member 3406 is illustrated as a ring-shape with a rectangular cross-section. The blocking member 3408 is illustrated as a relatively thin, sheet-like ring on a side of the diffusing member 3406 opposite the orifices 3402. The blocking member 3408 may be affixed to the diffusing member 3406 by any suitable means, for example by adhesive.

A cap 3422 is illustrated covering the diffusing member 3406 and the blocking member 3408. The cap 3422 may be in contact with the blocking member 3408 such that the diffusing member 3406 is compressed against the wall 3420. Alternatively, the diffusing member 3406 may not be compressed against the wall 3402. The cap 3422 may serve as the blocking member 3408, in which case the ring-shaped blocking member 3408 illustrated in FIG. 9C may be omitted.

The cap 3422 may include an angled, annular flange 3424 that may be spaced away from the wall 3420 to form an annular gap 3426. The annular flange 3424 may also be considered skirt-like or frusto-connical. The annular gap 3426 may provide a flow path to ambient atmosphere such that the flow of gas washout is not overly restricted. Alternatively, one or more openings (such as radial opening 3416) may be provided in the annular flange 3424 to provide a flow path to ambient atmosphere, which may also allow for elimination, in whole or in part, of the annular gap 3426.

The cap 3422 is illustrated with an annular groove 3428 mated with an annular protrusion 3430 to hold the cap 3422 in place. The annular protrusion may be continuous to form a snap fit or may be multiple, annularly spaced annular protrusions to provide a configuration that allows for minimal or no interference upon axial insertion followed by a twist to provide axial interference and hold the cap 3422 in place. In FIG. 9C, the annular protrusion 3430 is illustrated as three annularly spaced annular protrusions. A lip 3432 of the annular groove 3428 may be omitted in three corresponding locations and sizes to provide for reduced or no interference of the cap 3422 during the axial insertion. Other forms of attachment are possible. For example, a threaded fastening arrangement may be provided, the cap 3422 may be held in place with adhesive or welding. Releasable fastening such as the illustrated configuration or a threaded connection may allow for the diffusing member 3406 to be replaced if, for example, the diffusing member becomes damaged, clogged or dirty.

Although the vent 3400 is illustrated on one side of the bend (e.g., upstream with respect to an exhalation direction) in the elbow 3418, the vent 3400 may be upstream or downstream of the bend.

FIGS. 10A to 10C illustrate another alternate configuration of the vent 3400. Like reference numbers are similar to those described above and thus further description is omitted except as noted below. The vent 3400 in these figures is formed around an example of the decoupling structure 3500 that includes a ball 3434 and socket 3436 that are part of an elbow 3418. In the form illustrated here, the ball 3434 and socket 3436 allow three degrees of rotational freedom. However, fewer degrees of rotational freedom are possible, e.g., one or two degrees of rotational freedom.

As best viewed in FIG. 10D, the cap 3422 is connected by way of a snap fit connection 3438 with a first half 3440 located on the cap 3422 and a second half 3442 on the mating component. Six each of the first half 3440 and second half 3442 are provided between six of the radial openings 3416, three of which are visible in FIG. 10A. However, more or less may be provided as necessary to provide adequate retention and/or flow rate.

As best seen in FIG. 10C, forty-four orifices 3402 are illustrated equally spaced in a single annular row. However, the number and spacing of the orifices 3402 may take other configurations. For example, fewer orifices 3402 may be provided if, for example, lower flow rate is required or more orifices 3402 may be provided if, for example, greater flow rate is required. And as explained above, more rows may be provided. Also, the orifices need not be in an annular array. If, for example, the orifices are located other than in the illustrated location, the orifices may be arranged in a grid based on Cartesian coordinates. Alternatively, the orifices 3402 need not be in any type of row and may be located in random or pseudo random locations.

4.3.5 Decoupling Structure(s)

In one form the patient interface 3000 includes at least one decoupling structure 3500, for example, a swivel or a ball and socket.

4.3.6 Connection Port

Connection port 3600 allows for connection to the air circuit 4170.

4.3.7 Forehead Support

In one form, the patient interface 3000 includes a forehead support 3700.

4.3.8 Anti-Asphyxia Valve

In one form, the patient interface 3000 includes an anti-asphyxia valve.

4.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

4.4 Glossary

For the purposes of the present technology disclosure, in certain forms of the present technology, one or more of the following definitions may apply. In other forms of the present technology, alternative definitions may apply.

4.4.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Continuous Positive Airway Pressure (CPAP) therapy: CPAP therapy will be taken to mean the application of a supply of air to an entrance to the airways at a pressure that is continuously positive with respect to atmosphere. The pressure may be approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

4.4.2 Aspects of the Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Breathing effort will be said to be the work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: Preferably, a hypopnea will be taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal flow rate.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, airflow rate, patient airflow rate, respiratory airflow rate (Qr): These synonymous terms may be understood to refer to the RPT device's estimate of respiratory airflow rate, as opposed to "true respiratory flow" or "true respiratory airflow", which is the actual respiratory flow rate experienced by the patient, usually expressed in litres per minute.

Tidal volume (Ft): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of the inspiratory portion of one respiratory flow rate waveform and the start of the inspiratory portion of the following respiratory flow rate waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

4.4.3 RPT Device Parameters

Flow rate: The instantaneous volume (or mass) of air delivered per unit time.

While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. 'Flow rate' is sometimes shortened to simply 'flow'. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system. Respiratory flow rate, Qr, is the flow rate of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes in the patient interface.

Pressure: Force per unit area. Pressure may be measured in a range of units, including $cmH_2O$, $g-f/cm^2$, hectopascal. 1 $cmH_2O$ is equal to 1 $g-f/cm^2$ and is approximately 0.98 hectopascal. In this specification, unless otherwise stated, pressure is given in units of $cmH_2O$. The pressure in the patient interface is given the symbol Pm, while the treatment pressure, which represents a target value to be achieved by the mask pressure Pm at the current instant of time, is given the symbol Pt.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{12}$ watt.

Sound Pressure: The local deviation from ambient pressure at a given time instant as a result of a sound wave travelling through a medium. Sound pressure is usually given in decibels SPL, that is, decibels relative to a reference pressure, normally taken as $20 \times 10^{-6}$ Pascal (Pa), considered the threshold of human hearing.

4.4.4 Terms for Ventilators

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

EPAP: a base pressure, to which a pressure varying within the breath is added to produce the desired mask pressure which the ventilator will attempt to achieve at a given time.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

Ventilator: A mechanical device that provides pressure support to a patient to perform some or all of the work of breathing.

4.4.5 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage.

It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 4.4.6 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

4.4.7 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles.

The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

4.4.8 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a typically transparent thermoplastic polymer of Bisphenol-A Carbonate.

4.4.9 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or a rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls enclosing a volume of space, the volume having air therein pressurised above atmospheric pressure in use. A shell may form part of the walls of a mask plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie: A tie will be taken to be a structural component designed to resist tension.

Vent: (noun) the structure that allows an intentional flow of air from an interior of the mask, or conduit to ambient air, e.g. to allow washout of exhaled gases.

4.4.10 Terms Used in Relation to Patient Interface

Curvature (at a point on a surface): At each point, p, on the surface, there is a normal (e.g. a normal to an exterior surface). Each plane that contains the normal (a 'normal plane') cuts the surface and defines a curve. The curvature of that curve atp may be described as having a sign and a magnitude (e.g. 1/radius of a circle that just touches the curve atp). The directions of the normal plane where the curvature takes its maximum and minimum values are perpendicular, and are called principal directions. The principal curvatures atp are the curvatures in the principal directions.

Curvature (of a surface): A region of a surface having a saddle shape, which curves up in one direction and curves down in a different direction, will be said to have a negative curvature. A region of a surface having a dome shape, which curves the same way in two principal directions, will be said to have a positive curvature. A flat surface will be taken to have zero curvature.

Cylindrical region: A region of a surface including a path where each point in the region in the vicinity of the path has a zero curvature (or substantially zero curvature) tangential to the path, and a non-zero curvature in the orthogonal direction.

Dome region: A set of points on a surface whose principal curvatures have the same sign, e.g. both positive or both negative.

Edge (of a surface): A boundary or limit of a surface.

Floppy: A quality of a material, structure or composite that is one or more of:

Readily conforming to finger pressure.

Unable to retain its shape when caused to support its own weight.

Not rigid.

Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Intersection of two surfaces: A path where two surfaces meet.

Negative curvature: If the curve atp turns away from the normal, (e.g. concave down), the curvature in that direction at that point will be taken to be negative.

Path: In certain forms of the present technology, 'path' will be taken to mean a path in the mathematical—topological sense, e.g. a continuous function from $f(0)$ to $f(1)$ on a surface. In certain forms of the present technology, a 'path' may be described as a route or course, including e.g. a set of points on a surface.

Patient's point-of-view: The orientation of an object as it would be while in normal use by the patient.

Planar region: A region of a surface where the principal curvatures are zero (or near zero).

Positive curvature: If the curve atp turns towards the normal, (e.g. concave up), the curvature in that direction at that point will be taken to be positive.

Resilient: Able to deform substantially elastically, and to release substantially all of the energy upon unloading, within a relatively short period of time such as 1 second.

Ridge: A region of a surface where the curvatures in a first direction of each point is the region are non-zero, and similar in magnitude and sign.

Rigid: Not readily deforming to finger pressure, and/or the tensions or loads typically encountered when setting up and maintaining a patient interface in sealing relationship with an entrance to a patient's airways.

Surface label: Some physical structures in accordance with the present technology may comprise more than one surface. These surfaces may be distinguished using a label to describe an associated surface orientation, location, function, or some other characteristic. For example a structure may comprise one or more of an anterior surface, a posterior surface, an interior surface and an exterior surface. In another example, a cushion structure may comprise a face-contacting (e.g. outer) surface, and a separate non-face-contacting (e.g. underside or inner) surface. In another example, a structure may comprise a first surface and a second surface.

Semi-rigid: means being sufficiently rigid to not substantially distort under the effects of mechanical forces typically applied during respiratory pressure therapy.

Saddle region: A set of points on a surface where at each point in the set, the principal curvatures have opposite signs, that is, one is positive, and the other is negative.

Surface: A set of three-dimensional points traced out by two independently varying parameters, e.g., a sphere is parametrised by latitude and longitude.

4.5 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

PART LIST

1000 patient
1100 bed—partner
3000 patient interface
3100 seal—forming structure
3200 plenum chamber
3210 perimeter
3220 marginal edge
3300 structure
3400 vent
3402 outlet orifice
3404 wall
3406 diffusing member
3408 blocking member
3410 channel
3412 hole
3414 central hole
3416 radial opening
3418 elbow
3420 wall
3422 cap
3424 flange
3426 annular gap
3428 annular groove
3430 annular protrusion
3432 lip
3434 ball
3436 socket
3438 snap fit connection
3440 first half
3442 second half
3500 decoupling structure
3500 least one decoupling structure
3600 connection port
3700 forehead support
4000 RPT device
4170 air circuit
5000 humidifier

The invention claimed is:

1. A patient interface for sealed delivery of a flow of air at a continuously positive pressure with respect to ambient air pressure to an entrance to the patient's airways including at least an entrance of a patient's nares, wherein the patient interface is configured to maintain a therapy pressure in a range of about 4 cmH$_2$O to about 30 cmH$_2$O above ambient air pressure in use, throughout the patient's respiratory cycle, while the patient is sleeping, to ameliorate sleep disordered breathing, the patient interface comprising:
- a sealing structure configured to seal around the entrance to the patient's airways;
- a positioning and stabilising structure to maintain the sealing structure in sealing contact with an area surrounding the entrance to the patient's airways while maintaining a therapeutic pressure at the entrance to the patient's airways;
- a plenum chamber configured to be pressurised at a pressure above ambient pressure in use;
- a gas washout vent configured to allow patient-exhaled CO$_2$ to flow to an exterior of the plenum chamber to minimise rebreathing of exhaled CO$_2$ by the patient, the gas washout vent including one or more outlet orifice each defining a first axis;
- a diffusing member covering each of the one or more outlet orifice; and
- a blocking member having an air-impermeable material, the blocking member preventing all gas exiting from each of the one or more outlet orifice from flowing through the diffusing member and from exiting the diffusing member in a same direction as the one or more outlet orifice and including at least one hole through the blocking member, the at least one hole defining a second axis,
wherein the first axis and the second axis are not aligned and not parallel.

2. The patient interface according to claim 1, wherein the diffusing member and the blocking member are configured to direct the gas exiting from the one or more outlet orifice outward from the diffusing member in an orientation different than the one or more outlet orifice.

3. The patient interface according to claim 1, wherein the diffusing member provides a flow path parallel to a surface of the blocking member that is in contact with the diffusing member.

4. The patient interface according to claim 1, wherein the diffusing member is a porous material.

5. The patient interface according to claim 1, wherein the diffusing member is an open cell foam.

6. The patient interface according to claim 1, wherein the diffusing member is fibrous material.

7. The patient interface according to claim 1, wherein the blocking member is fixed to the diffusing member along a surface of the blocking member that contacts the diffusing member.

8. The patient interface according to claim 7, wherein the surface of the blocking member is opposite the one or more outlet orifice with respect to a thickness of the diffusing member.

9. The patient interface according to claim 1, wherein the gas washout vent comprises a plurality of the outlet orifice.

10. The patient interface according to claim 1, wherein the first axis defined by a center of each of the one or more outlet orifice is not perpendicular to a nearest surface of the diffusing member.

11. The patient interface according to claim 1, wherein the air-impermeable material is a flexible material.

12. The patient interface according to claim 1, wherein the air-impermeable material is a rigid material.

13. The patient interface according to claim 1, further comprising a channel configured to allow liquid to drain away from the one or more outlet orifice.

14. The patient interface according to claim 13, wherein the one or more outlet orifice is in the channel.

15. The patient interface according to claim 14, wherein the channel has a V-shaped or U-shaped cross-section.

16. The patient interface according to claim 15, wherein the one or more outlet orifice is in a leg of the V-shaped or U-shaped cross section.

17. The patient interface according to claim 1, wherein the at least one hole of the blocking member is configured to redirect the gas exiting from the one or more outlet orifice.

18. The patient interface according to claim 17, wherein the blocking member comprises a plurality of the hole, the plurality of the hole includes multiple orientations of the plurality of the hole that are configured to redirect the gas in multiple directions.

19. The patient interface according to claim 1, wherein the diffusing member and the blocking member are removably attached to the plenum chamber.

20. The patient interface according to claim 1, wherein the first axis and the second axis form an angle between 15 and 75 degrees.

21. The patient interface according to claim 1, wherein the gas washout vent comprises a plurality of the outlet orifice and the blocking member comprises a plurality of the hole.

22. The patient interface according to claim 1, wherein the first axis of each of the one or more outlet orifice forms an acute angle with a surface of the plenum chamber.

23. The patient interface according to claim 22, wherein the acute angle is between 15 and 75 degrees.

24. The patient interface according to claim 1, wherein the one or more outlet orifice extends through a wall of the plenum chamber, and the first axis is not perpendicular to a surface of the wall of the plenum chamber.

* * * * *